United States Patent
Aylott et al.

(10) Patent No.: US 6,331,438 B1
(45) Date of Patent: Dec. 18, 2001

(54) OPTICAL SENSORS AND MULTISENSOR ARRAYS CONTAINING THIN FILM ELECTROLUMINESCENT DEVICES

(75) Inventors: Jonathan W. Aylott; Zoe Chen-Esterlit, both of Ann Arbor, MI (US); Jon H. Friedl, Ames, IA (US); Raoul Kopelman, Ann Arbor, MI (US); Vadim N. Savvateev; Joseph Shinar, both of Ames, IA (US)

(73) Assignees: Iowa State University Research Foundation, Inc., Ames, IA (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/448,499

(22) Filed: Nov. 24, 1999

(51) Int. Cl.$^7$ ..................................... G01N 21/64
(52) U.S. Cl. .................... 436/172; 422/82.07; 422/82.08
(58) Field of Search .............................. 250/458.1, 459.1; 436/172; 422/82.05, 82.07, 82.08

(56) References Cited

U.S. PATENT DOCUMENTS

| | | | |
|---|---|---|---|
| 3,725,658 | * 4/1973 | Stanley et al. . | |
| 4,539,507 | 9/1985 | VanSlyke et al. . | |
| 4,720,432 | 1/1988 | VanSlyke et al. . | |
| 4,769,292 | 9/1988 | Tang et al. . | |
| 4,885,211 | 12/1989 | Tang et al. . | |
| 5,157,262 | * 10/1992 | Marsoner et al. | 250/458.1 |
| 5,247,190 | 9/1993 | Friend et al. . | |
| 5,334,539 | 8/1994 | Shinar et al. . | |
| 5,352,906 | 10/1994 | Shinar et al. . | |
| 5,361,314 | 11/1994 | Kopelman et al. . | |
| 5,399,502 | 3/1995 | Friend et al. . | |
| 5,512,490 | 4/1996 | Walt et al. . | |
| 5,517,313 | 5/1996 | Colvin, Jr. . | |
| 5,577,137 | * 11/1996 | Groger et al. | 385/12 |
| 5,703,436 | 12/1997 | Forrest et al. . | |
| 5,774,603 | 6/1998 | Moore et al. . | |
| 5,807,627 | 9/1998 | Friend et al. . | |
| 5,821,690 | 10/1998 | Martens et al. . | |
| 5,849,351 | 4/1999 | Colvin, Jr. . | |
| 5,879,630 | 3/1999 | Lescouzeres et al. . | |
| 5,891,398 | 4/1999 | Lewis et al. . | |
| 5,910,661 | 6/1999 | Colvin, Jr. . | |
| 6,051,437 | 4/2000 | Luo et al. . | |
| 6,077,712 | 6/2000 | Livingston . | |
| 6,093,308 | 7/2000 | Lewis et al. . | |
| 6,107,083 | 8/2000 | Collins et al. . | |
| 6,117,686 | 9/2000 | Tanaka et al. . | |
| 6,136,611 | 10/2000 | Saaski et al. . | |
| 6,197,258 | 3/2001 | Thompson et al. . | |
| 6,241,948 | 6/2001 | Watkins et al. . | |
| 6,254,829 | 7/2001 | Hartmann et al. . | |
| 6,254,831 | 7/2001 | Barnard et al. . | |

FOREIGN PATENT DOCUMENTS

| | | |
|---|---|---|
| 0 549 345 A2 | 6/1993 | (EP) . |
| 0 569 827 A2 | 11/1993 | (EP) . |

OTHER PUBLICATIONS

Antson, H. et al "Characterization of Thin–Film Electroluminescent Structures by SIMS and other Analytical Techniques" Fresenius Z. Anal. Chem. vol. 322, pp. 175–180 (1985).*

(List continued on next page.)

*Primary Examiner*—Jeffrey Snay
(74) *Attorney, Agent, or Firm*—Dickstein Shapiro Morin & Oshinsky LLP

(57) ABSTRACT

Optical sensor, probe and array devices for detecting chemical biological, and physical analytes. The devices include an analyte-sensitive layer optically coupled to a thin film electroluminescent layer which activates the analyte-sensitive layer to provide an optical response. The optical response varies depending upon the presence of an analyte and is detected by a photodetector and analyzed to determine the properties of the analyte.

90 Claims, 16 Drawing Sheets

OTHER PUBLICATIONS

Freemantle; "Downsizing Chemistry", Science Technology, Feb. 22, 1999, pp. 27–36.

FOXY Fiber Optic Oxygen Sensors; www.oceanoptics.com/ProductsSheets/FOXY.asp; 18 total pages.

Chen–Esterlit et al; "Development of oxygen and pH optical sensors using phase modulation technique"; Proc. SPIE vol. 3540, pp. 19–27, Chemical, Biochemical, and Environmental fiber Sensors X, Robert a. Lieberman; Ed., abstract.

Tang et al.; "Organic electroluminescent diodes"; Appl. Phys. Lett. 51 (12), 21, Sep. 1987, pp. 913–915.

Tang et al; "Electroluminescence of doped organic thin films"; J. Appl. Phy. 65 (9), May 1, 1999, pp. 3610–3616.

Shaheen et al.;"Bright blue organic light–emitting diode with improved color purity using a LiF/Al cathode", J. Appl. Phy., vol. 84, No. 4, Aug. 15, 1998, pp. 2324–2327.

O'Brien et al.; "Improved energy transer in electrophosphorescent devices", Appl. Phys. Lett. vol. 74, No. 3, Jan. 18, 1999, pp. 442–444.

Carraway et al.; "Photophysics and Photochemistry of Oxygen Sensors Based on Luminescent Transition–Metal Complexes"; Anal. Chem. vol. 63, No. 4, Feb. 15, 1991, pp. 337–342.

Xu et al.; "Oxygen Sensors Based on Luminescence Quenching of Metal Complexes: Osmium Complexes Suitable for Laser Diode Excitation"; Anal. Chem. vol. 58, No. 15, Aug. 1, 1996, pp. 2605–2609.

O'Keefe et al.; "Development of a LED–based Phase fluorimetric oxygen sensor using evanescent wave excitation of a sol–gel immoblized dye"; Sensors and Actuators B 29 (1995), pp. 226–230.

Castellano et al.; "A Water–Soluble Luminescence Oxygen Sensor", Photochemistry and Photobiology, 1998, 67(2), pp. 179–183.

Shortreed et al.; "Development of a fluorescent optical potassium–selective ion sensor with ratiometric response for intracellular applications", Sensors and Actuators B 38–39 (1997), pp. 8–12.

Shortreed et al.; "Miniature Sodium–Selective Ion–Exchange Optode with Fluorescent pH Chromoionophores and Tunable Dynamic Range", Anal. Chem. vol. 68, No. 15, 1996, pp. 2656–2662.

Barker et al.; "Nitrite– and Chloride–Selective Fluorescent Nona–Optodes and in Vitro Application to Rat Conceptuses", Anal. Chem. vol. 70, No. 1, 1998, pp. 100–104.

Lakowicz; "Topics in Fluorescence Spectroscopy", vol. 1 Techniques, Chapter 5, pp. 293–299.

Lakoxicz; "Topics in Fluorescence Spectroscopy", Chapter 3, pp. 51–75.

Li et al.; "Fabrication and electroluminescence of double–layered organic light–emitting diodes with the $Al_2O_3$/AI cathode", Appl. Phys. Lett. 70 (10), Mar. 10, 1997, pp. 1233–1235.

Li et al.; "Effects of aquaregia treatment of indium–tin–oxide substrates on the behavior of double layered organic light–emitting diodes", Appl. Phys. Lett. 70 (20), May 19, 1997, pp. 2741–2743.

Tang et al.; "Bright high efficiency blue organic light–emitting diodes with $Al_2O_3$/AI cathodes", Appl. Phys. Lett 71 (18), Nov. 3, 1997, pp. 2560–2562.

Service; "Your (Light–Emitting) Logo", Science Magazine, 279 (5354) 1135b, 5 total pages. www.sciencemag.org/cgi/content/full/279/5354/1135b.

Borman; "Fiber–Optic Sensors: Device measures pH inside single cells", News of the Week, Nov. 2, 1992 C&EN.

Tannas; "Flat–Panel Displays and CRTs", 1985, pp. 1, 16–17.

Roubi; Science Technology, Jun. 23, 1997, C&EN.

Preliminary Specifications, "19.6 mm (0.77–inch) SXGA Monochrome OLED image Source" AFED Corporation, 3 total pages.

Service; "Patterning electronics on the Cheap"; Science Magazine, 278 (5337); 383, 3 total pages. www.sciencemag.org/cgi/content.

Lieberman; "Organic LEDs take display confab by a 'nose'."; EE Times, Apr. 1, 1999; San Jose, California.

Watkins et al; "Portable, Low–Cost, Solid–State Luminescence–Based $O_2$ Sensor", Applied Spectroscopy, vol. 52, No. 5, 1998, pp. 750–754.

Dickinson et al; "Convergent, Self–encided Bead Sensor Arrays in the Design of an Artificial Nose"; Analytical Chemistry, vol. 71, No. 11, Jun. 1, 1999, pp. 2192–2198.

Cornell et al.; "A blosenor that uses ion–channel switches"; Nature, vol. 387, Jun. 1997, pp. 580–583.

Forrest et al.; "Making light of it"; 5 total pages.

Sobel; "Television's Bright New Technology"; Scientific American, May 1998, pp. 70–77.

Bulovic et al.; "Transparent light–emitting devices"; Nature vol. 380 Mar. 7, 1996, p. 29.

D. Lieberman, *Electronic nose, other novel apps seen for Organic LEDs;* http://web5.infortrac.galegroup.com/itwi/l; accessed Jul. 19, 2001.

*Reseachers Build Electronic Nose;* http://ask.elibrary.com/printdoc.asp?; accessed Jul. 19, 2001.

*Universal Display Corporation Annouces DARPA Program Funding for Flexible OLED Displays Increased to $3 million;* http://www.universaldisplay.com/newsroom.php?pr=2001–06–28a; accessed Jul. 27. 2001.

*Patents Licensed from Princeton University and University of Southern California for which UDC has the Exclusive Right to sub–license;* http://www.universaldisplay.com/ip-.php; accessed Jul. 27, 2001.

*Mimicking the Sense of Olfaction: Development of a Conducting Polmer Composite–Based Electronic Nose;* http://ww.arpa.mil/ato/programs/uxo/html/cit_abstract.html; accessed Aug. 2, 2001.

N. Lewis; *Electronic Nose;* http://www.gbnet.com/surf/surf96/cce.Lewis.html; accessed Aug. 2, 2001.

*The Caltech Electronic Nose Project:* http://www.micro-.caltech.edu/muri/1998/sld001.htm; accessed Aug. 2, 2001.

M. Blanco, et al.; *Molecular Modeling of Polymeric Chemical Sensors: The Artificial Nose;* http://www.wag-.caltech.edu/muri/1998/sld001.htm; accessed Aug. 2, 2001.

* cited by examiner

OPTICAL SENSORS AND MULTISENSOR ARRAYS CONTAINING THIN FILM ELECTROLUMINESCENT DEVICES

GOVERNMENT RIGHTS

The United States Government has certain rights in this invention pursuant to Contract Number W-7405-Eng-82 between the Department of Energy and Iowa State University, and pursuant to Grant Numbers MDA 972-97-0006 and RO1GM50300 between the University of Michigan and DARPA and the University of Michigan and the National Institutes of Health, respectively.

FIELD OF THE INVENTION

The field of this invention is thin film electroluminescent device ("TFELD")—activated optical sensors, probes, and integrated multiprobe and multisensor arrays for detecting and quantifying biological, chemical, and physical analytes.

BACKGROUND OF THE INVENTION

Detection and quantification of analytes are of prime interest in medical, biochemical, analytical chemical, occupational safety, microelectronic, environmental, military, and forensic applications. Optical sensing and probing is an alternative to electrochemical sensors, which consume analytes, have long response times, have limitations for in vivo use, and are susceptible to poisoning by various contaminants. Various studies on optical methods of analyte detection have been reported in which a dye is immobilized in an analyte-permeable layer. In particular, these studies include sensors whose photoluminescence ("PL") is affected by the analyte. Such affects may include a change in the PL intensity, spectrum, decay time, or polarization.

Commercially available optical sensors typically employ inorganic single crystal III-V compound LEDs as the light source. However, the need to incorporate optical components to convey light to the sensor and to collect the PL for readout increases complexity, size, and costs. Single crystal GaN-based inorganic LEDs also are incompatible with silicon technology, and thus do not permit fabrication of integrated multisensor arrays.

U.S. Pat. No. 5,517,313 relates to an optical sensor using a P-N junction as a light emitting diode. The LED is placed in an indicator layer which is analyte permeable and contains indicator molecules. The presence of analyte alters the amount of light emitted from the indicator molecules. The emitted light is incident upon a photodetector. The amount of current from the photodetector depends upon the incident light, which is used to detect the analyte. U.S. Pat. No. 5,894,351 relates to an optical sensing device which includes a light-emitting P-N junction having a hole in a direction perpendicular to the P-N junction plane. Upon application of an electrical potential across the junction, light is emitted from the junction into the hole. The hole contains an analyte-permeable fluorescent matrix. A photodetector at one end of the hole generates an electrical signal responsive to light emitted by the fluorescent matrix. P-N junction LEDs, however, are typically prepared from materials that are not compatible with existing silicon technologies and thus do not permit fabrication of integrated multisensor arrays. In addition, P-N junction LEDs cannot be made transparent to allow compact and simple sensor devices that utilize "back detection" to collect the PL signal. Further, P-N junction LEDs are fabricated at temperatures that are too high for integration with temperature-sensitive organic and biochemical sensor materials.

Various multicolor thin film electroluminescent ("EL") devices are known in the art. For, example, U.S. Pat. Nos. 4,356,429, 4,539,507, 4,720,432, 4,769,292, 4,885,211, and 5,703,436 and European Patents 92311760.0 and 93107241.7 relate to organic electroluminescent devices ("OLED"). Thin film electroluminescent devices ("TFELD"), such as the OLEDs mentioned above and in, e.g., U.S. Pat. Nos. 5,352,906, 5,821,690, 5,399,502, and 5,807,627, have been known for use in display applications. However, to date no disclosure exists relating to the use of TFELDs to activate optical sensors or probes, much less any recognition of the surprising advantages which the present inventors have achieved by the use of TFELDs in new optical sensing and probing technologies.

SUMMARY OF THE INVENTION

What is needed are optical sensors, probes, and multisensor arrays capable of monitoring, quantifying, and analyzing analytes in real-time, which are easy to use, have high sensitivity and specificity, and also are inexpensive to the point of being disposable.

The present invention provides optical sensors, probes and integrated multisensor and multiprobe arrays for measuring a diverse range of biological, chemical, and physical analytes. The sensors, probes, and arrays include an analyte-sensitive layer optically coupled to a thin film electroluminescent device. The TFELD may be deposited on one surface of a glass or other suitable transparent substrate. The other surface of the substrate supports a sensor layer such that the sensor layer, e.g., a polymeric matrix containing dye molecules, can be exposed to the analyte. The sensor layer and TFELD are thus in face-to-face configuration on opposite sides of the substrate. The TFELD is connected to a power source to activate electroluminescence ("EL") from a luminescent thin film layer of the TFELD. This EL excites the sensor layer to provide an optical response. The optical response varies depending upon the presence of an analyte. The response is detected by a photodiode, CCD array, or other suitable photodetector, and analyzed to determine the properties of the analyte.

The invention also provides arrays containing large numbers of sensor pixels and corresponding TFELDs (collectively called "sensor units") prepared on-chip in microelectronic configurations. The ability to manufacture TFELD-activated optical sensor units of small lateral dimensions via silicon technology provides a special advantage for "lab-on-a-chip" applications of the invention. The TFELD-activated sensor units of the present invention are easily prepared as an array of several thousand devices on a small transparent substrate. Existing technology allows for deposition of sensor units onto a 400×400 $mm^2$ substrate with a system throughput greater than 10 substrates per hour. The cost of materials is also minute in comparison to Group III-V compound single crystal-activated sensors and the deposition conditions are much more lax. In addition, the sensor units of the invention can also be readily integrated with microdisplay technologies.

Use of TFELDs, such as organic light emitting devices ("OLED"), permits the construction of sensors that utilize back detection of the signal by, for example, employing optically transparent TFELDs. By "back detection" herein we mean that the photodetector is located on the same side of the substrate as the TFELD; the secondary light (PL) emitted by the sensor or probe, which carries the information concerning the analyte, passes through the TFELD. The devices of the invention are preferably fabricated to allow back detection through a transparent light source. This configuration and the face-to-face coupling of EL into the sensor layer and other advantages of the present invention permit small size, ease of manufacture, low cost, and facilitate the fabrication and use of thin-film sensing arrays on-chip in microelectronic configurations.

A specific embodiment of the present invention relates to a miniature solid-state oxygen sensor. The sensor layer may be, e.g., a thin film of tris(4,7-biphenyl-1,10-phenanthroline) Ru(II) chloride ("Ru(dpp)") immobilized within a porous sol-gel matrix, the photoluminescence (PL) intensity and decay time ("lifetime") of which are quenched by molecular oxygen. The Ru(dpp) sensor layer may be applied directly onto the back surface of a blue OLED or other TFELD, which provides pulsed or continuous excitation for the Ru(dpp).

Other specific embodiments of the invention relate to optical biosensors which utilize sensing strategies and indicator systems for sensing ionic species, nucleotides, antibodies, enzymes, and other biologically active moieties. These aspects of the invention provide TFELD-activated ion correlation sensors, enzymatic sensors, immunosensors, and molecular beacons, as will be discussed in greater detail hereinbelow.

Specific applications of the invention include, for example, disposable, integrated OLED/probe or sensor dosimeters, small and active enough that a person can wear them and obtain a status reading at any time. Real-time readout obviates the need to send a measuring device to a lab for analysis. If a person is exposed to a harmful environment, curative action can be taken at once, rather than waiting for receipt of the analysis results. The sensing chemistry can be selected to depend on the pathogens or other analytes to which the worker is likely to be exposed and multiple hazardous substances can be monitored simultaneously. In addition, the disposable integrated probe or sensor is easily replaceable.

By "integrated" herein we mean that the preferred devices of the invention are constructed such that the TFELD light source and the sensor layer are juxtaposed such that each sensor unit is comprised of two or more thin film layers (analyte-sensitive sensor layer and TFELD) working together as a monolithic sensor unit. Unless indicated otherwise, the terms "sensor," "multisensor," "sensing" and "sensor units" herein include "probes," "multiprobe," "probing" and "probe units," respectively, and vice versa.

In another specific application of the invention, a user of protective clothing can obtain real-time information on the condition of the clothing. The safety rating provided for protective clothing assumes that the garment is not damaged. The invention provides miniature probe or sensor devices that can be placed in a gas mask or other protective gear to measure the atmosphere within them. Should the composition of the air change and become dangerous, a real-time warning is given by the device and corrective action can be taken. Potential users include fire fighters, personnel handling pollutants, medical or biomedical personnel, and the military. In addition, disposable sensors are provided to form a "first aid sensor kit" to be applied to and around the location of a suspected spill or other contamination of, e.g., a microelectronics clean room, pharmaceutical, or other facility, to rapidly detect, localize and remove sodium, various chlorine- or fluorine-based acids, or other hazardous contamination, thus preventing production line shutdown and ensuing losses. In still another application, law enforcement personnel may be equipped with a kit of low-cost disposable slip sensors to permit detection of the presence or absence of residues of gun powder, illicit drugs, explosives, or alcohol vapors on the body, clothes, or belongings of a suspect or victim. Similarly, combat soldiers and medics maybe provided with a "personnel protection kit" to check the presence or absence of chemical or biological warfare agents, radioactive contamination in the air, aerosoles, contaminated surfaces of buildings, vehicles, ammunition, weapons, or poisons in drinking water and food supplies.

These and other advantages and features of the invention will be more readily understood from the following detailed description which is provided in connection with the accompanying drawings.

DETAILED DESCRIPTION OF PREFERRED EMBODIMENTS

The optical probing and sensing devices and methods of the present invention combine thin layer probing and sensing chemistries and light sources (TFELDs), which may be arranged face-to-face in contact with each other or on the opposite sides of a transparent substrate. Alternatively, the probe or sensor layer may be deposited directly on the TFELD. The probe or sensor is exposed to the analyte, while the light source is preferably sealed from the analyte by the substrate or a suitable sealant layer.

Each probe or sensor unit contains a selective indicator molecule, compound, or other agent for reaction with an analyte or ligand of interest in a sample. The probe or sensor relies upon the optical response generated by the selective indicating agent for detecting and determining the presence of a single analyte or ligand in the sample. For detection of multiple analytes or ligands, a series of different probe or sensor units with individual specificities are used together. The specific optical signal generation of the probe or sensor can be accomplished using a variety of different indicator agents, including colorimetric or fluorescent dyes, selective polymer films, or biological receptors such as enzymes and antibodies. In each instance, at least one probe or sensor unit is provided for the detection of each analyte or ligand of interest. Some of the sensor units may also use indicator agents which serve as an internal reference and do not change their optical response in the presence of any analyte. Individual sensing elements may be paired with individual TFELDs, preferably selected such that the absorption coefficient of the indicator agent and/or sensor layer is relatively high at the emission peak of the selected TFELD.

Figure 1:
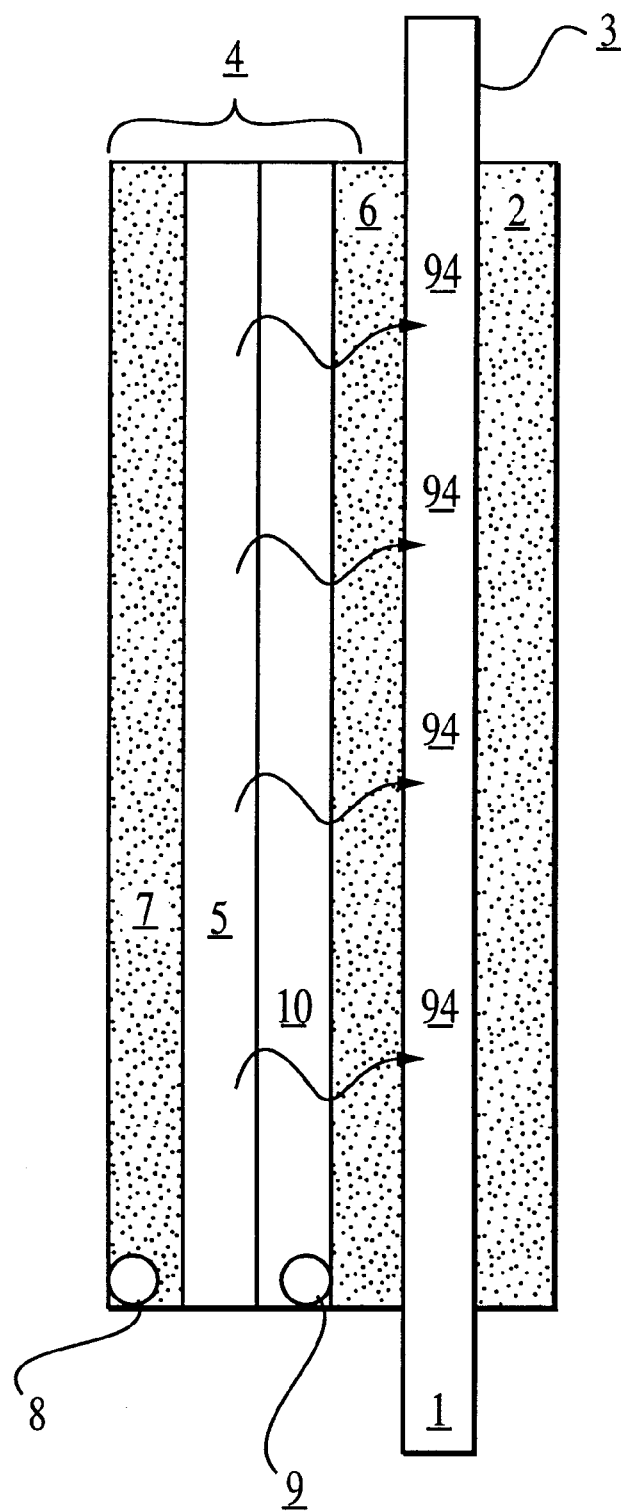
FIG. 1 shows a schematic of an integrated OLED probe or sensor according to the invention.

As shown in FIG. 1, each probe or sensor unit typically includes a transparent substrate 1, which has a probe or sensor layer 2 applied to its upper surface 3. The opposite surface of substrate 1 supports a TFELD generally shown as 4, including luminescent layer 5, and two electrodes, i.e., anode 6 and cathode 7. In operation, a negative bias, from wire 8, is applied to the cathode 7 and a positive bias, from wire 9, is applied to anode 6, thus causing luminescent layer 5 to radiate electroluminescent light 94 of a predetermined wavelength through substrate 1 and into sensor layer 2. Sensor or probe layer 2 emits an optical response to the electroluminescent wavelength and such response is dependent upon the presence, quantity, or absence of a particular analyte in the sample or environment to which the probe or sensor layer 2 is exposed. The analyte may be detected by measuring the wavelength, intensity, and/or decay lifetime of the optical response of probe or sensor layer 2.

Each probe or sensor layer 2 comprises a thin film formed by, for example, a polymeric matrix, support, or other carrier, and an indicator agent such as a dye, and typically appears as a discrete film having a thickness ranging from about 0.01–1,000 microns, a thickness of between 0.5–15 microns being most preferred. The thin films themselves may be either transparent or translucent. Since a thickness of 0.01–1,000 microns is permissible, the thinner films demonstrate no substantial optical density (i.e., absorbance).

The thin film probing or sensing layer 2 typically has a regular geometric form, substantially flat and smooth. Alternative physical configurations, however, are envisioned and intended; such alternatives would include physical configurations shaped as hairs, sleeves, wells, or cavities, and irregularly shaped and textured embodiments specific to their applications. The flexibility and tensile strength of the thin film may vary and will depend upon the polymeric or other matrix or carrier material used. These variances are provided and controlled by the user's particular choice of composition from among, for example, various known polymer compositions and by choice of cross-linking concentration, functional group modifications, and the like.

The supporting substrate 1 may also take any size, configuration, or appearance, may be geometrically regular or irregular and may be composed of one or any variety of different materials, e.g., glasses, plastics, or composites. As shown in FIG. 1, the supporting substrate 1 is a translucent or transparent article such that light may pass through it. In other applications, an optically active material such as a color filter or a polarizer may be used as substrate 1. In addition to using transparent or translucent substrates for fixing and immobilizing the sensing units, it is also possible to use various flexible plastic sheets or optical fibers as the supporting substrate. The supporting substrate 1 serves as a physical location and/or a guide to the PL and EL emissions for each of the probe or sensor layers 2 and TFELDs 4.

The probe or sensor units may be fabricated by first manufacturing a complete thin film entity (probe or sensor and/or TFELD) which is then attached to the surface of the supporting substrate using a suitable adhesive, sonic welding, or other means of attachment. Alternatively, the probe or sensor layer and/or TFELD may be individually cast or deposited and formed in-situ directly on the surface of the supporting substrate. For example, a dye compound and various monomers may be combined in admixture and then polymerized in place directly on the external surface to form the thin film probe or sensor layer 2 of the sensing unit. The TFELD 4 may likewise be prefabricated and then attached, or deposited layer by layer upon substrate 1.

Thin film electroluminescent devices convert electrical energy into electromagnetic radiation through the use of a cathode, anode, and a luminescent active layer. Typically they are less than about $1\mu$ in thickness. Unlike P-N junction LEDs, which are single-crystal devices, TFELDs may be low or high voltage, single crystal, polycrystalline, or amorphous, may be prepared as extended area devices and operated by carrier injection or by capacitive coupling. TFELDs can be inorganic solid-state devices which will typically emit radiation in the visible region to the near infrared, i.e., in a region of about 400–1300 nm. Generally, an inorganic solid-state TFELD includes elements from Groups IIB, IIIA, IVA, and VA of the Periodic Table of the Elements. For example, the TFELD can be made of polycrystalline zinc sulfide (ZnS) or selenide (ZnSe). TFELDs can be based on organic molecules as well. Because of the high photoluminescence quantum yields of various $\pi$-conjugated molecules and polymers, light emission through charge injection under a high applied field (injection EL) is possible. For example, $Alq_3$, DPVB1, and $\pi$-conjugated polymers such as the poly(3-alkylthiophenes) (P3ATs), poly(p-phenylenevinylenes) (PPVs), poly(p-phenylenes) (PPPs), and their ladder type derivatives, and poly(alkylfluorenes), and polymers derived from these, can comprise the active luminescent layer of the TFELD. Most preferably, the TFELD of the sensor unit is at least 90% transmissive at 400 nm or longer wavelengths. That is, the TFELD is preferably essentially colorless.

As shown in FIG. 1, TFELD 4 comprises an anode 6 on substrate 1 of, for example, glass or a flexible plastic. Anode 6 typically comprises a coating of, for example, indium tin oxide, polyaniline, or copper phthalocyanine (CuPc), on which is deposited a hole-transporting layer 10. In a particularly preferred embodiment, hole transporting layer 10 comprises a first and second hole transporting layer, the first such layer preferably being made of 4,4',4"-tris(N-(3-methoxyphenyl)-N-phenyl-amine-triphenylamine) ("3-AS"), MTDATA, or CuPc, and the second hole transporting layer being made of N,N',biphenyl-N,N'-bis(3-methylphenyl)-(1,1'-biphenyl)-4,4'-diamine ("triphenyl diamine") ("TPD"). Either or both hole transporting layers may also comprise N,N'-biphenyl-N,N'-bis(1-naphthyl)-1,1'-biphenyl-4,4'-diamine ("alpha-NPD"). See, e.g., C. W. Tang, et al., "Organic Electroluminescent Diodes," Appl. Phys. Lett. 51, 913–915 (1987); C. W. Tang, et al., "Electroluminescence of Doped Organic Thin Films," J. Appl. Phys. 65, 3610–3616 (1989); S. E. Shaheen, et al., "Bright Blue Organic Light Emitting Diode with Improved Color Purity Using a LiF/Al Cathode," J. Appl. Phys. 84, 2324 (1998); and D. F. O'Brien, et al., "Improved Energy Transfer in Electrophosphorescent Devices," Appl. Phys. Lett. 74, 442 (1999). Electron transporting layer 5 is deposited on hole-transporting layer 10, one or preferably both of layers 5 and 10 being light-emitting and comprising a thin-film of less than 1 $\mu$. Electron transporting layer 5 preferably comprises 8-tris-(hydroxy quinoline) Al ("Alq$_3$") (green emitter), amino oxadiazolefluorene ("AODF") (blue emitter), 4,4'-bis(2,2'-biphenylvinyl)-1,1'-biphenyl ("DPVBi") (blue emitter), 4,4'-N,N'-dicarbazolyl biphenyl ("CBP") (host for guest-host blue emitting layers), or distyrylarylene ("DSA") (blue to red emitters). See, e.g., C. W. Tang, et al., "Organic Electroluminescent Diodes," Appl. Phys. Lett. 51, 913–915 (1987); C. W. Tang, et al., "Electroluminescence of Doped Organic Thin Films," J. Appl. Phys. 65, 3610–3616 (1989); S. E. Shaheen, et al., "Bright Blue Organic Light Emitting Diode with Improved Color Purity Using a LiF/Al Cathode," J. Appl. Phys. 84, 2324 (1998), D. F. O'Brien, et al., "Improved Energy Transfer in Electrophosphorescent Devices," Appl. Phys. Lett. 74, 442 (1999). Cathode 7, preferably a thin film of lithium fluoride, or cesium fluoride, followed by Al, or Mg$_{0.9}$ Ag$_{0.1}$, is deposited on layer 5, and wires 8, 9 connect the TFELD to a power source. When the power source is turned on, holes generated at anode 6 are transported to the interface between layers 5 and 10 where they combine with electrons transported from cathode 7, generating visible radiation 94.

The TFELD structure of the probe or sensor units of the invention may be constructed using various suitable processes. Each layer of the TFELD may be constructed or applied, for example, via ink jet printing, solution coating, or evaporation. As used herein, "evaporation" includes all forms of deposition from the vapor phase, including but not limited to vacuum deposition. Typically, vacuum sublimation and spin coating are used in the fabrication of such devices.

The devices according to the invention may be constructed using various different light transmission geometries. The direct transmission geometry is shown schematically in FIG. 2. However, it may be modified, e.g., by fabricating the TFELD in a ring or horseshoe geometry (FIG. 3) or with a transparent TFELD (FIG. 4) to permit detection of the analyte in back detection mode. Back detection geometries are particularly preferred for multisensor matrices in which any individual TFELD of an array of sensor units can be powered each time, providing the ability to collect an individual signal from a particular sensor unit.

Figure 2:
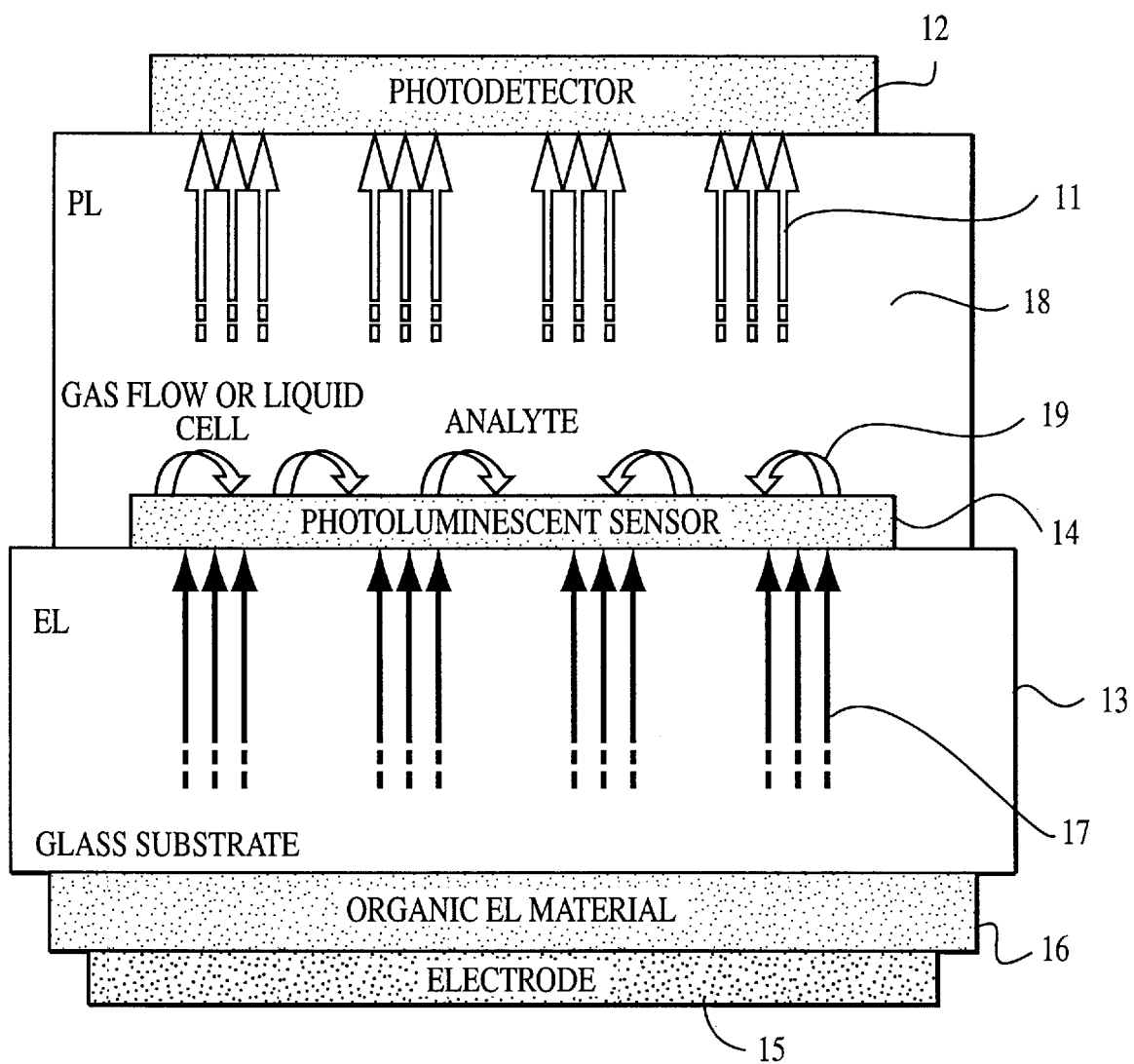
FIG. 2 depicts an optical sensor according to the invention which has a direct transmission geometry.

The schematic shown in FIG. 2 depicts a direct transmission embodiment of the invention wherein spectral response 11 is collected for analysis by a photodetector 12 located on the same side of the substrate 13 as sensor layer 14. Cathode 15 causes electroluminescent layer 16 to emit light 17 across substrate 13 and into probe or sensor layer 14. Probe or sensor layer 14 is exposed to an analyte-containing medium 18, such as a gas or liquid, such that analyte 19 interacts with probe or sensor layer 14 to alter its optical characteristics. The optical response 11, as a result of emitted light 17 and analyte 19, is detected by photodetector 12.

Figure 3:
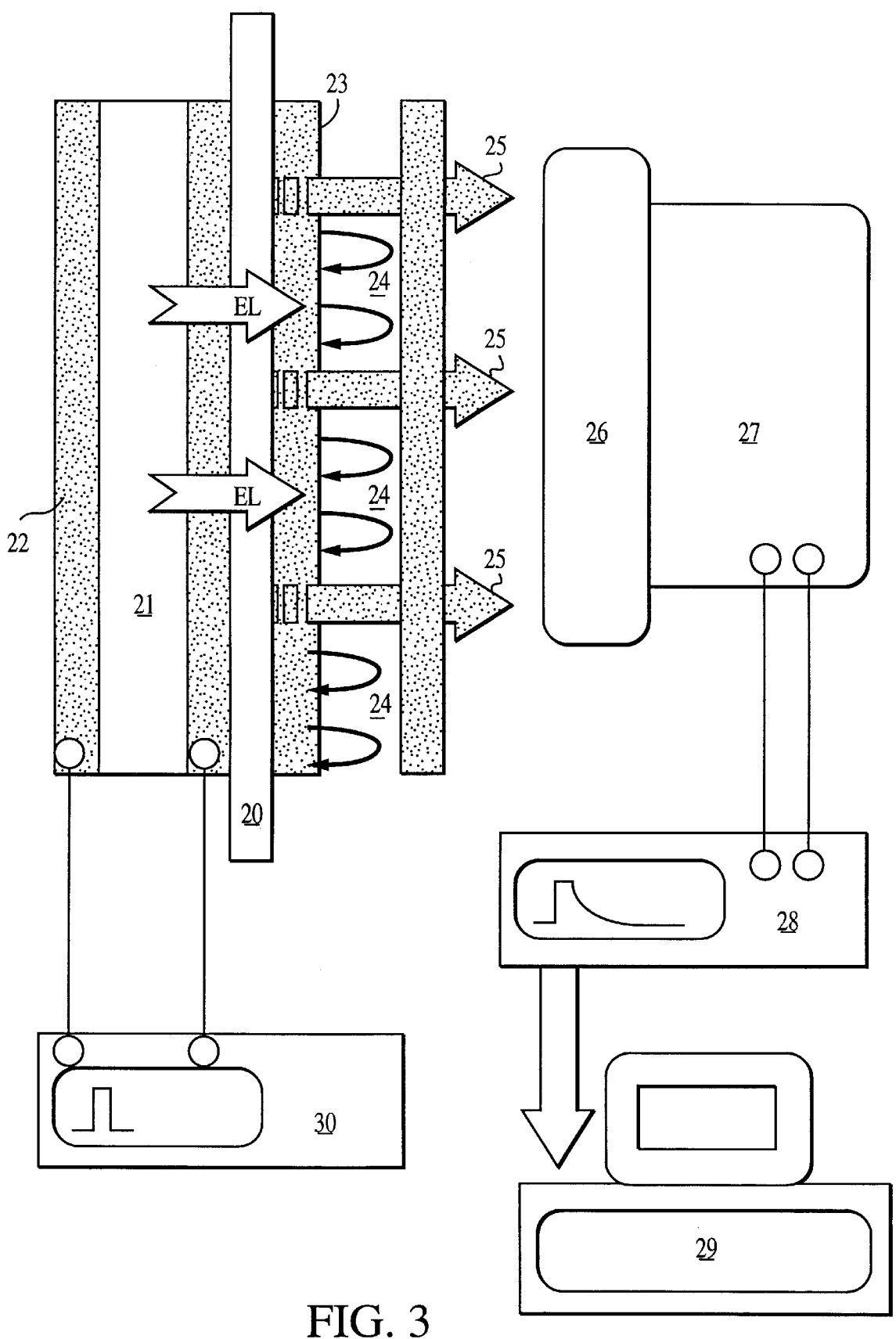
FIG. 3 shows a schematic of the EL and PL light pathways of the sensor of FIG. 2.

The direct transmission embodiment is also shown in FIG. 3. FIG. 3 shows a device containing a substrate 20, and an electroluminescent layer 21 with electrode 22. Sensor layer 23 is deposited on the opposite side of substrate 20 so that the electroluminescent and sensor layers 21 and 23 are in face-to-face configuration. The sensor layer 21 is exposed to analyte as shown schematically by arrows 24, and emits PL as shown schematically by arrows 25. PL 25 passes through filter 26 for filtering out any undesired light. The PL 25 is then collected by a photodetector 27, such as a Si photodiode, avalanche photodiode ("APD"), a photomultiplier tube (PMT), a CCD-based detector, charge injection device ("CID"), or a CMOS based imager, which transmits signals to readout device 28, such as an oscilloscope, for electrical readout. Computer 29 analyzes the transmitted signal from the readout device 28. Device 28 and electrode 22 are in electrical communication with pulse generator 30. Pulse generator 30 excites electroluminescent layer 21 with a pulsed bias to allow time-resolved analyte detection, in other words, fluorescence life-time detection based on operating the TFELD in a pulsed mode.

Pulsed mode operation can provide certain advantages over intensity based measurements. Since the fluorescent lifetime of the indicator agent is an intrinsic property, it offers the possibility of inherent referencing and avoids calibration errors that can sometimes occur in connection with some intensity based measurements. Using phase modulation techniques, as described, for example, in J. R. Lakowicz, "Measurement of Fluorescence Lifetimes" in "Principles of Fluorescence Spectroscopy;" Plenum Press, Berlin (1983), and J. R. Lakowicz and I. Gryczynski, "Frequency-domain fluorescence spectroscopy," in "Topics in Fluorescence Spectroscopy," Volume 1: Techniques, Ed. By J. R. Lakowicz, pp. 293–355, Plenum Press, New York (1991), the indicator is excited with a continuous, sinusoidally modulated light source. Because of the finite lifetime of the excited state of the dye or other indicator agent, the emission is delayed in time relative to the modulated excitation and as a result it is phase shifted. See, also, F. N. Castellano, et al., "Water-soluble Luminescence Oxygen Sensor," Photochemistry and Photobiology, 67(2), pp. 179–183 (1998); G. O'Keeffe, et al., "Development of a LED-based phase fluorimetric oxygen sensor using evanescent wave excitation of a sol-gel immobilized dye," Sensors and Actuators; B Chem. 29, pp.226–230 (1995); W. Xu, et al., Anal. Chem. 68, pp. 2605–2609 (1996); E. R. Carraway, et al., "Photophysics and Photochemistry of Oxygen Sensors Based on Luminescent Transition-metal Complexes," Anal. Chem. 63, pp. 337–342 (1991); Z. Chen-Esterlit, et al., "Development of Oxygen and pH Optical Sensors Using Phase Modulation Technique," SPIE Proc., 1999, 3540, pp. 19–27. The results of Example II, below, demonstrate integrated sensor devices operated in time resolved, i.e., lifetime-based, mode. Preferably, the decay lifetime of the pulsed TFELD is at least one order of magnitude shorter than the shortest decay time of the probe or sensor.

Figure 4:
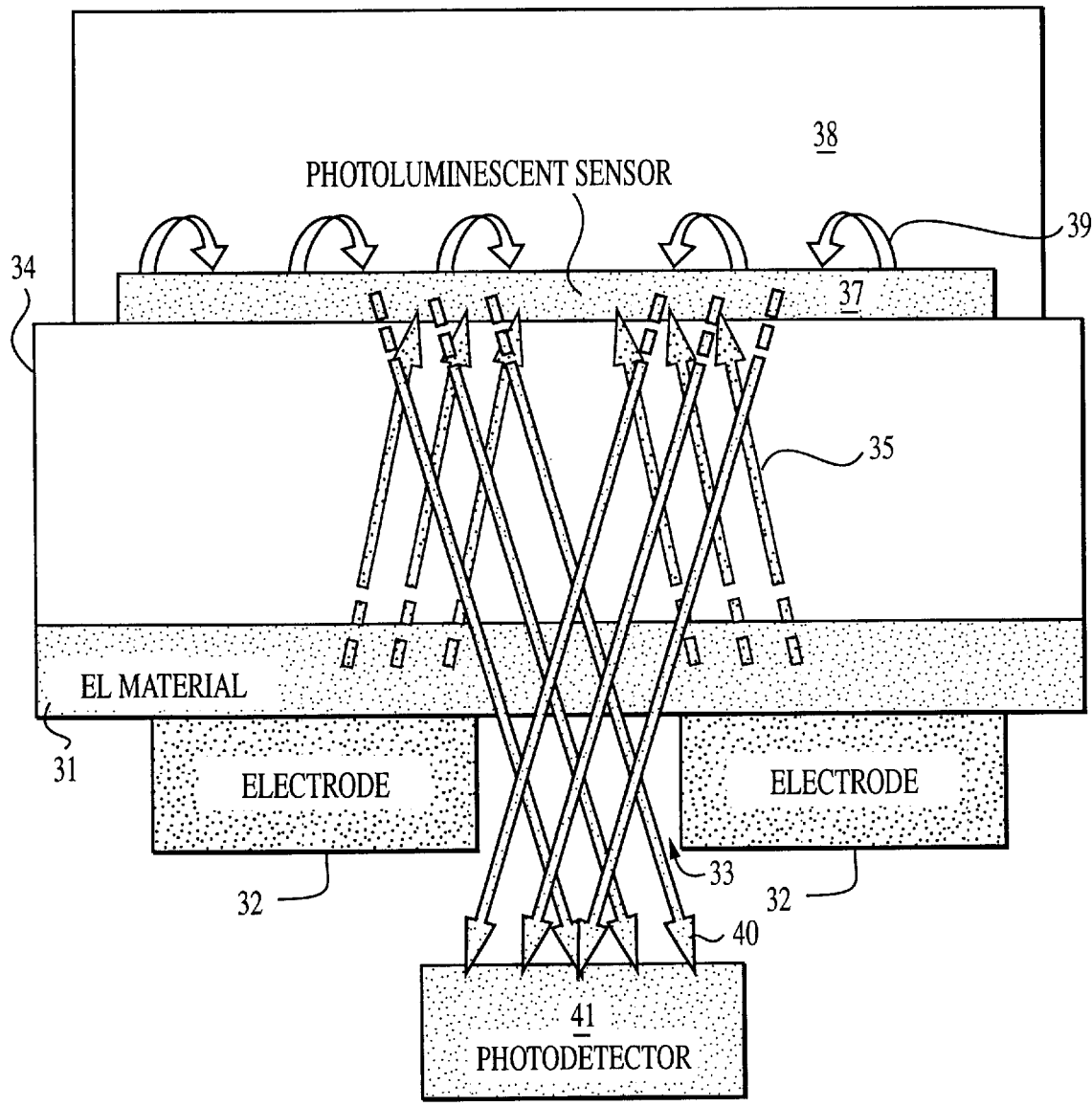
FIG. 4 depicts an optical sensor according to the invention which has a ring or horseshoe geometry, resulting in back detection of the PL.

FIG. 4 shows a schematic of the sensor of the invention in one of several potential back detection geometries. More specifically, the schematic shows electroluminescent layer 31 having cathode 32 containing an opening 33 on one side of a transparent substrate 34. EL 35 is emitted from layer 31 through a transparent anode (not shown) and substrate 34 into a photoluminescent probe or sensor layer 37. Probe or sensor layer 37 is exposed to medium 38 with analyte 39, which causes a different PL 40 from sensor layer 37 than if analyte 39 was not present. PL 40 travels back through substrate 34, electroluminescent layer 31, and through opening 33 of cathode 32, to be collected by photodetector 41.

Figure 5:
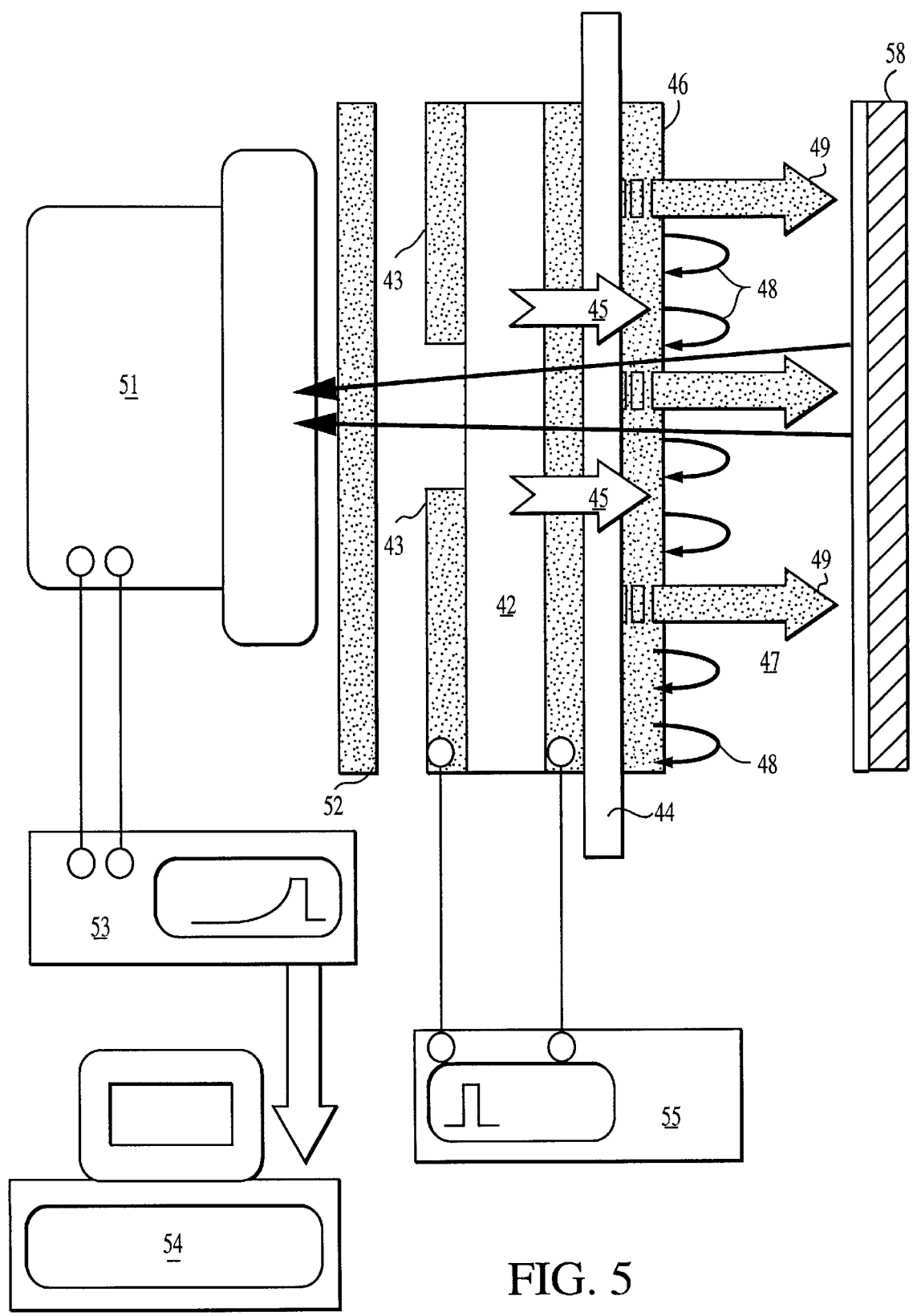
FIG. 5 shows a schematic of the EL and PL light pathways of the sensor of FIG. 4.

A system according to the invention for time-resolved back detection is shown in FIG. 5. FIG. 5 shows electroluminescent layer 42 having spaced apart electrodes 43 on one side of a transparent substrate 44. Electroluminescence 45 is emitted in pulsed mode from layer 42 through substrate 44 into photoluminescent sensor layer 46. Sensor layer 46 is placed within a gas or liquid 47 with analyte, shown schematically by arrow 48, which causes a different photoluminescent emission 49 from sensor layer 46 than if analyte 48 was not present. Photoluminescent emission 49 is reflected by mirror 50 back through substrate 44, electroluminescent layer 42, and between electrodes 43, and collected by photodetector 51. An optical filter 52 is disposed between substrate 44 and photodetector 51 to filter out light of a wavelength other than photoluminescent emission 49. An oscilloscope 53, computer 54, and pulse generator 55 are in electrical communication to permit pulsed electroluminescent excitation of sensor film 46 and allow time-resolved analyte detection.

Figure 6:
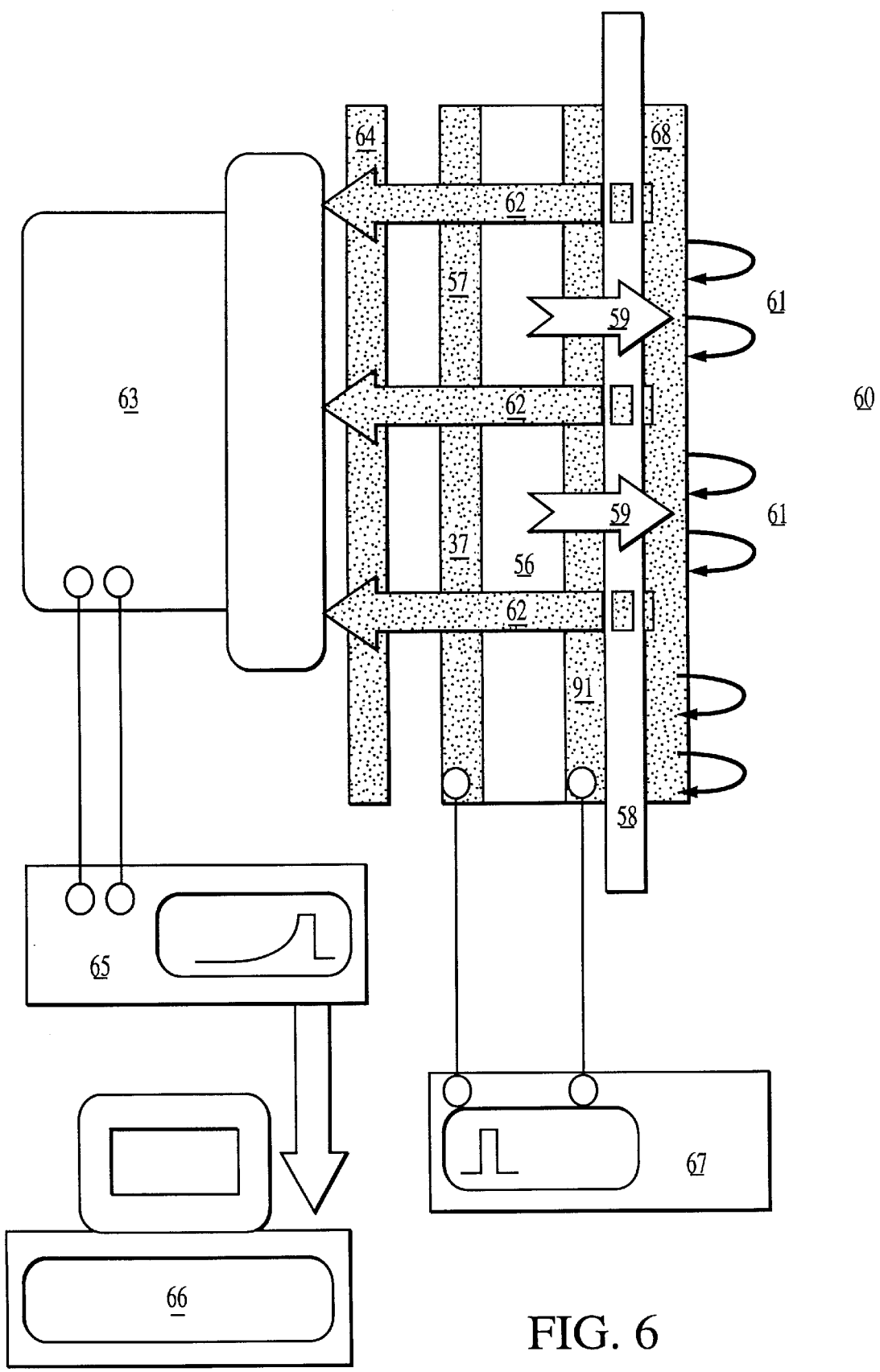
FIG. 6 depicts a sensor according to the invention in back detection mode utilizing a transparent TFELD.

Another system for time-resolved back detection is shown in FIG. 6. In FIG. 6, electroluminescent layer 56 is sandwiched between transparent electrodes 57 and 91 on one side of a transparent substrate 58. EL 59 is emitted in a pulsed mode from layer 56 through substrate 58 into photoluminescent sensor layer 68. Probe or sensor layer 68 is disposed within a gas or liquid 60 with analyte, shown schematically by arrows 61, which cause a different photoluminescent emission 62 from sensor layer 68 than if analyte 61 was not present. PL 62 travels back through substrate 58, electroluminescent layer 56, and transparent electrodes 57 and 91, to be collected by photodetector 63. An optical filter 64 is disposed between substrate 58 and photodetector 63 to filter out light of a wavelength other than PL 62. The system of FIG. 6 also includes oscilloscope 65, computer 66, and pulse generator 67 in electrical communication so as to permit pulsed electroluminescent excitation of sensor layer 68. The system also includes an optional mirror 69.

Figure 7:
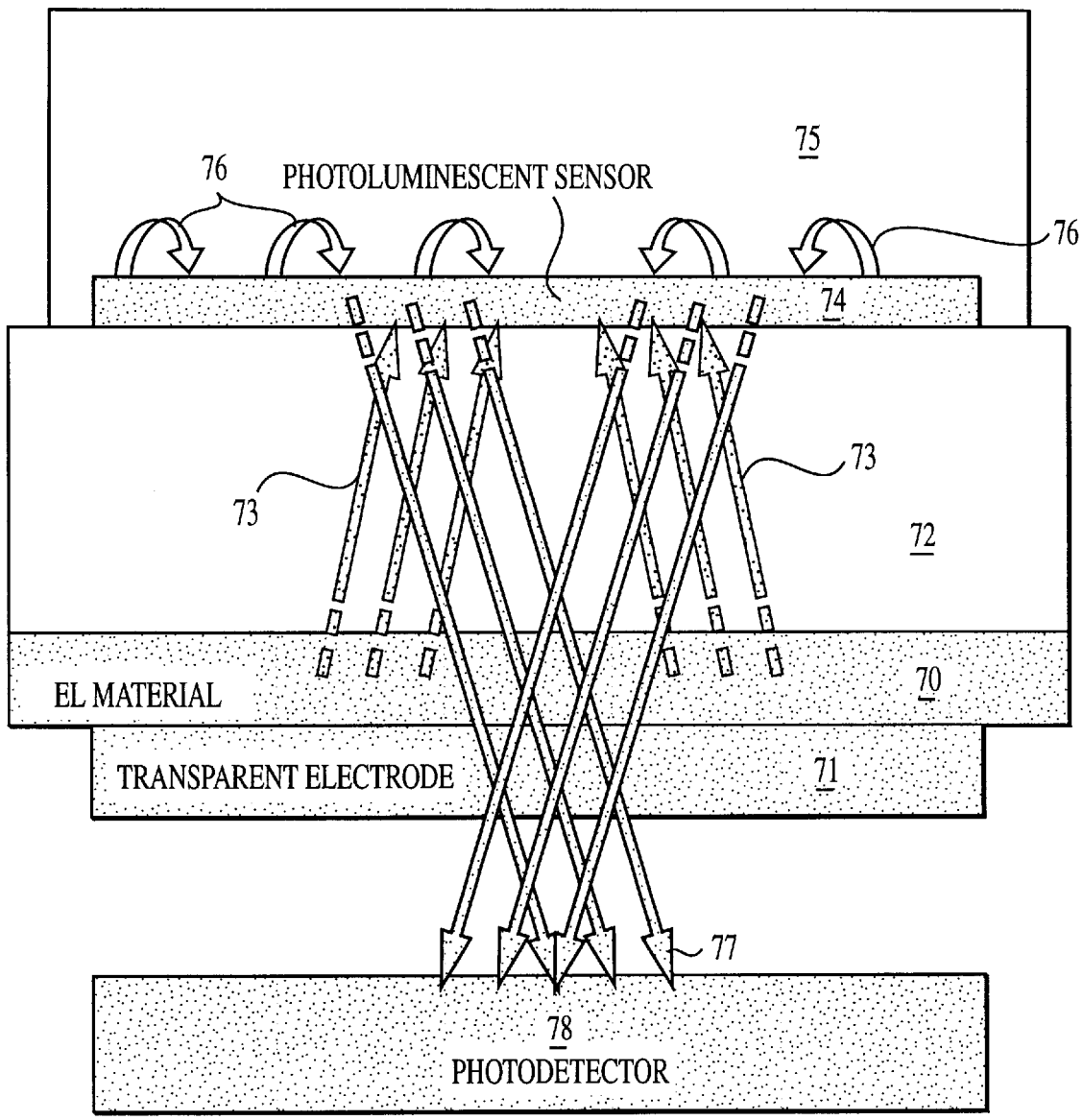
FIG. 7 shows a schematic of the EL and PL light pathways of the sensor of FIG. 6.

FIG. 7 shows a schematic of the probe or sensor of FIG. 6. The schematic shows an electroluminescent layer 70 having transparent electrodes 71 on one side of a transparent substrate 72. EL 73 is emitted from layer 70 through substrate 72 into photoluminescent sensor layer 74. Sensor layer 74 is disposed within gas or liquid 75 with analyte 76, which causes a different PL 77 from sensor layer 74 than if analyte were not there. PL 77 travels back through substrate 72, electroluminescent layer 70, and transparent electrode 71, to be collected by photodetector 78.

The present invention also provides optical arrays of thin film probing or sensing units whose combinations of probe or sensor layer indicator agents and matrix or other carrier materials, if present, may be varied to meet a particular application or usage and selected for detecting a group or specific class of analytes expected to be encountered in the intended circumstances. Accordingly, a variety of known compositions and compounds which are unique for or indicative of a physical circumstance or location, a hazardous or toxic problem, or a clinical or environmental need, may be detected by reaction with the array of multiple sensing units of the optical sensor. Thus, a variety of different sensor layers containing different indicator agents can be incorporated in an appropriate carrier or matrix, e.g., polymers, sol-gels, and silicones, so that a range of analytes can be detected in a multi-sensor array. The array may also include various light sources with different excitation wavelengths, utilizing, for example, the tunable range of TFELDs or stacked OLEDs over the complete spectral range. The face-to-face configuration between the sensor layer and the TFELD not only assures strong coupling of the EL into the sensor film but also reduces or prevents crosstalk between neighboring pixels.

Figure 8:
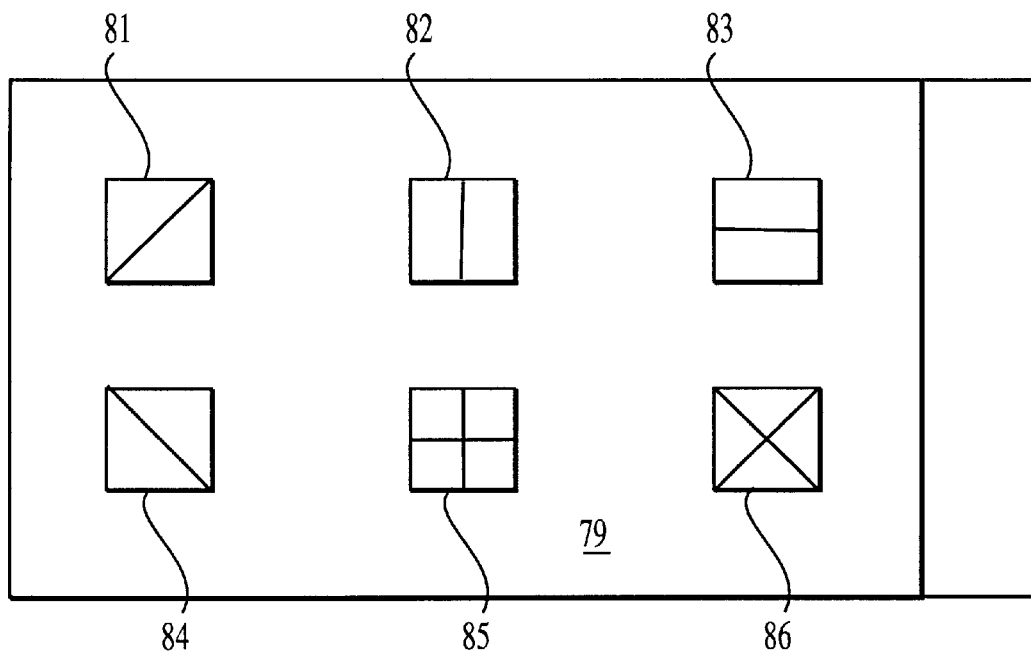
FIG. 8 depicts a multisensor array according to the invention.
Figure 8:
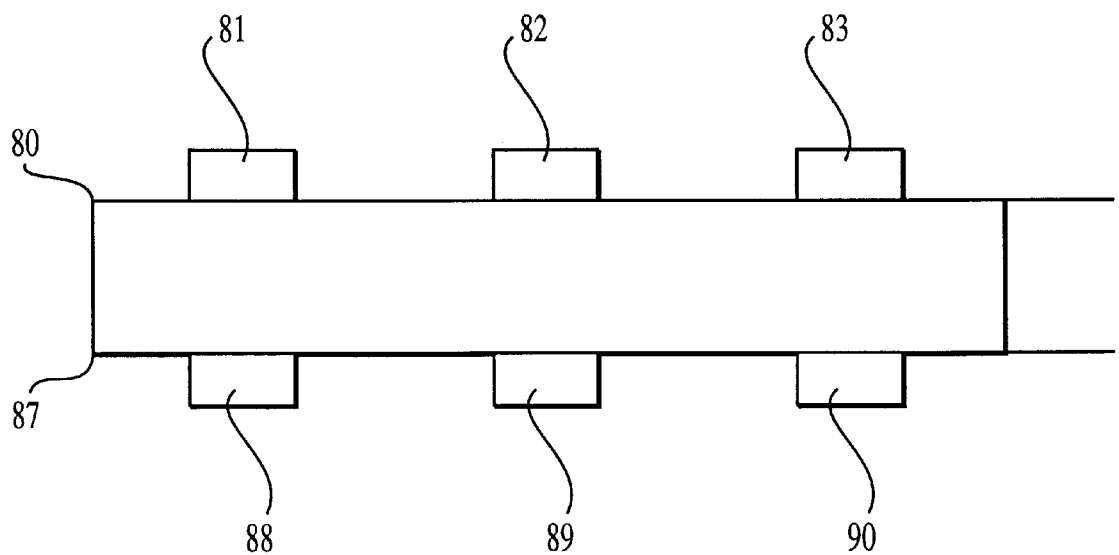

FIG. 8 shows a sensor array in a highly simplistic format. A substantially rectangular supporting substrate 79, which can be flexible or rigid, is shown having a substantially flat surface 80. Deposited upon the surface 80 are a plurality of thin film sensing layers 81, 82, 83, 84, 85 and 86, respectively. More than one sensing unit of the same type (chemical formulation) may be employed; each type of sensing layer is formulated differently as a thin film and has its own unique combination of a carrier or matrix substance and indicator molecule, compound, or other agent with specific spectral properties. In each sensing layer, the indicator agent, in the absence of any analyte or mixture of ligands, is able to absorb light energy of at least one wavelength and will yield a spectral response which is optically detectable and recognizable. On the opposite side of substate 87 there are TFELDs 88, 89, and 90, one TFELD corresponding to each sensor layer and having a predetermined emission wavelength selected so as to excite the desired spectral response of each respective sensor layer in the presence of analyte.

Such sensor arrays are particularly well-suited for scaled up production and are readily fabricated using existing IC technologies. Using microfabrication techniques, the sensing layers and TFELD devices can be integrated directly onto a micro-chip which contains the circuitry for analogue signal conditioning/processing and data analysis. This provides for the production of millions of different sensor units in a single manufacturing step using, for example, ink-jet technology. Controlled compositional gradients in the sensor units of an array can be induced in a method analogous to how a color ink-jet printer deposits and mixes multiple colors. Rather than multiple colors, a plurality of different indicator agents and carriers are used. A sensor array of a million distinct elements only requires a 1 cm×1 cm sized chip employing lithography at the 10 $\mu$m resolution level, which is within the capacity of conventional commercial processing and deposition methods. The sensors can then be integrated onto a microprocessor to efficiently feed the data stream directly into a neural network, software, or hardware, and analysis section. The TFELD-activated sensor array may be powered by any suitable electric source, including, for example, one or more thin batteries, which may be laminated to the array.

An array for detecting a complex variety or mixture of analytes in a fluid may be fabricated by electrically coupling the sensor leads of an array of compositionally different sensor units to an optical measuring device. The device measures changes in spectral response, wavelength, intensity, or decay lifetimes, at each sensor unit of the array, preferably simultaneously and preferably over time. The device may include signal processing means in conjunction with a computer for qualitative and quantitative analysis. Typically such an array comprises at least ten, usually at least 100, and often at least 1000 different sensors.

Sensor measurements may be performed using the multisensor array apparatus shown schematically in FIG. 8 in a variety of suitable ways, including, but not limited to, the following manner. Excitation light is transmitted and illuminates each sensing layer in the array which individually fluoresces in proportion to analyte concentration. The fluorescent light is then detected by, for example, a CCD array or camera. The CCD array or camera typically contains photosensitive elements coupled to an electronic intensifier, which in turn is connected to a computer having a graphic card that digitizes and processes the output of the CCD array or camera. It may also contain one or more optical filters for spectral discrimination, and to reduce cross-talk between neighboring sensors and improve signal detection. In certain applications (e.g., inside protective clothing), the detection may be carried out with a photographic color film which is processed later (e.g., for measuring the total dosage of a harmful chemical to which the worker was exposed).

The optical sensing apparatus and instrumentation detects changing fluorescence either as changes in light intensity or changes in light wavelength over time, i.e., an optical response progression generated by and released from each individual sensing unit after initial illumination with light energy of a pre-determined wavelength which is then absorbed by the indicator agent in each thin film sensor layer. The light energy emitted from each sensing unit (in the presence of and in the absence of a ligand or analyte of interest) is collected by the CCD array or camera using various suitable frame grabbing technologies and image processing capabilities which can readily be selected by one of ordinary skill given the teachings herein.

Various indicator agents for use in the sensor layer are known and commercially available. The present invention intends that all of the various classes of photoluminescent or π-conjugated materials can be employed as needed or desired for the specific use or application. Merely illustrative of the many different dye materials are those fluorophores and chromophores listed below in Tables 1 and 2, respectively.

TABLE 1

| Fluorophores | Excitation Wavelength (range or maximum) | Fluorescence emission range (max) |
| --- | --- | --- |
| Eosin | 520–530 nm | 530–580 nm (550 nm) |
| TRITC-amine | 555 nm | 570–610 nm (590 nm) |
| Quinine | 33–352 nm | 382–450 nm |
| Fluorescein W | 488–496 nm | 530 nm |
| Acridine Yellow | 464 nm | 500 nm |
| Lissamine Rhodamine B Sulfonyl Chloride | 567 nm | 580 nm |
| Erthroscein | 504 nm | 560 nm |
| Ruthenium (tris, bipyridium) | 460 nm | 580 nm |
| Texas Red Sulfonyl Chloride | 596 nm | 615 nm |
| B-phycoerythrin | 545 m 565 nm | 575 nm |
| Nicotinamide adenine Dinocleotide (NADN) | 340 nm | 435 nm |
| Flavin adenine Dinucleotide (FAD) | 450 nm | 530 nm |
| Carboxy Seminaphthorhodafluor | 587 nm | 640 nm |
| Naphthofluorescein | 594 nm | 663 nm |

TABLE 2

| Chromophores | Range (max) |
| --- | --- |
| Iron-salicylate complex | 530 nm |
| Indamine dye | 590 nm |
| INT formazon dye | |
| Hopkins-Cole dye | 560 nm |
| Quinome-imine dye | 500 nm |
| $Fe(SCN)^{+2}$ | 460 nm |
| Malachite Green | 620 nm |
| 4-bromo A-23187, | 340 nm |

TABLE 2-continued

| Chromophores | Range (max) |
| --- | --- |
| Cresol red | 415 nm, acid; 570 nm, base |
| Biphenylcarbazone Disulphonic acid | 575 mn |
| Chrome bordeaux B | 575 nm |
| Calmagite | 650 nm |
| Ninhydrin dye | 650 nm |

As a specific illustrative example, the Ruthenium complexes belong to a family of oxygen-sensitive fluorophores and dyes that undergo collisional quenching of PL intensity and lifetime by molecular oxygen. These complex fluorophores are photostable and produce electronically excited states which have long lifetimes (~100 ns to several microseconds) and high quantum yields. For example, the PL yield of tris(4,7-biphenyl-1,10-phenanthroline)Ru(II) chloride ("Ru(dpp)") is about 30% and it is readily quenched by oxygen.

Table 3 shows the quantum yields for a variety of fluorescent dyes that are responsive to representative analytes pH, calcium and oxygen. Of the listed dyes, Ru(dpp) has the highest quantum yield of the oxygen-selective dyes. The other fluorescent dyes, however, have even higher quantum yields. The sensors of the invention can therefore be made to detect any chosen analyte, provided an appropriate analyte-sensitive indicator agent or system is chosen. Selection of appropriate indicator agents and systems for specific analytes is well within the level of skill of those in the art, given the teachings herein.

TABLE 3

| Fluorescent Dye | Quantum Yield | Analyte |
| --- | --- | --- |
| BCPCF | 0.83 | PH |
| BCECF | 0.84 | |
| Fluorescein | 0.92 | |
| Ca Green-1 | 0.75 | Ca |
| Oregon Green BAPTA-1 | ~0.7 | |
| Indo-1 | 0.56 | |
| Fura-2 | 0.49 | |
| Ru(dpp) | 0.30 | $O_2$ |
| PtOEPK | 0.12 | |
| $Ru(bpy)_3$ | 0.042 | |

Each light energy absorbing formulation or composition suitable for use will react with each analyte or ligand of interest which is present either alone or in admixture with other entities. Each indicator agent will then show evidence of such reactive contact by either absorbing and reflecting a portion of the light energy or, alternatively, by absorbing light energy and then emitting light energy of a different wavelength. Such reflected or emitted light energy is conveyed from the sensor layer for detection and measurement by light intensity, lifetime, or wavelength.

Individual analytes or ligands can be detected and identified as single chemical compounds when present in a liquid or gaseous sample. Alternatively, blends or admixtures of different analytes or ligands in one sample can also be identified as a mixture of distinct entities or chemical species. In addition, the component compounds of entirely novel chemical compositions and formulations never previously characterized may be analyzed to yield detectable features on analyte information using the sensor units of the present invention.

The range and diversity of analytes or ligands which may be detected and identified, singly or in combination, by the present invention includes noxious organic and inorganic compounds in liquid or gaseous form which are volatile in nature; toxic and non-toxic gases; environmental pollutants in air, water, and soil; and any matter which can be dispersed, disaggregated, suspended, or otherwise carried in a fluid medium. A representative listing, includes, for example, molecular oxygen, ionic species such as calcium and potassium, aromatic compounds such as benzene and toluene, thiols, alkanes, alkenes, alkynes and other hydrocarbon species, esters, alcohols, amines, aldehydes, ketones, carboxylic and other acids, biologically active moieties such as antibodies, enzymes, nucleotides, proteins, and microbes, including, but not limited to viral particles and bacteria, as well as physical analytes, such as pressure and pH. In general, any physical, chemical or biological entity which can be made to interact either directly or indirectly with an indicator agent, for example, a dye and/or polymeric matrix surrounding a dye compound, so as to impact the optical characteristic of the agent is detectable by the devices and methods of the invention.

In particular situations an indicator agent may not be available that has the desired selectivity, specificity, or reversibility. In such situations it is more applicable to utilize sensing strategies and indicator systems that can encompass a wide range of dyes and/or sensor layers. Thus, in addition to various fluorescent dyes sensitive to analytes described previously, other sensing strategies are available for detecting a wide variety of analytes, including, for example, ionic sensors, enzymatic sensors, immunosensors, and molecular beacons. The choice of matrix or other carrier or substrate is dependent on the molecule or other indicator agent to be immobilized and the sensing strategy employed. Matrices include, for example, sol-gel glasses, polyacrylamide, PVC, and decyl methacrylate Two general formats for polymeric matrix substances include a fully prepared polymer or copolymer, existing in bulk as a polymerized composition, and reagent materials such as monomers, co-monomers, cross linkers and the like which are combined into a reaction mixture and then polymerized in-situ by any suitable technique to yield a polymeric substance. Either mode of polymeric substance is suitable for use in making a matrix for indicator compounds of the sensing layer. Substrates that can be used for enzyme immobilization, in particular, include, e.g., PVA and glutaraldehyde.

The strategy for ion correlation sensors to detect, e.g., $Na^+$, $K^+$, $NO_2^-$, and $Cl^-$, is that an ionophore (selective to the ion of interest), a chromoionophore (generally a pH sensitive dye) and a lipophilic additive are co-immobilized in a matrix, e.g., PVC or decyl methacrylate. When an ion of the analyte of interest is present it complexes with the ionophore, resulting in the association or disassociation of an $H^+$ ion with the chromoionophore and a change in fluorescence. The lipophilic additive is present to maintain the ionic strength in the sensor layer. By selection of particular ionophores and chromoionophores the dynamic range of the sensor unit can be tuned to the desired concentration range as shown, for example, in Table 5. In addition, the chromoionophore can be substituted with a voltage sensitive dye, e.g., Merocyanine 540, RH 421 and di-8-ANEPPS, which will measure the change in potential within the matrix when the ion of interest complexes with the ionophore. The change in potential will be reported as a change in the fluorescence of the voltage sensitive dye. See Krause et al., Anal. Chem., 1999, 71, 1544–1548.

TABLE 5

| Analyte | Ionophore | Chromo-ionophore | Additive | Reference |
|---|---|---|---|---|
| $K^+$ | BME-44 | ETH 2439 | KTFPB | 1 |
| $Na^+$ | 1,3 bridged calix[4] crown Na ionophore | ETH 5294 | KTFPB | 2 |
| $NO_2$ | Cyanoaquacobyrinic acid Heptakis (2-phenylethylester) | ETH 5350 | KTFPB | 3 |
| $Cl^{1-}$ | Indium(III) octaethyl porphyrin chloride | ETH 2439 | KTFPB | 3 |

[1] M. R. Shortreed, S. K. Dourado, R. Kopelman, Sens. Act. B, 38–39, (1997), 8–12.
[2] M. R. Shortreed, E. Bakker, R. Kopelman, Anal. Chem., 68, (1996), 2656–62.
[3] S. L. R. Barker, B. A. Thorsrud, R. Kopelman, Anal. Chem., 70, (1998), 100–104.

With regard to enzymatic sensors, the principle behind oxidase based optical biosensors used to monitor analytes, such as glucose and lactate, is that the enzyme specific to the analyte is co-immobilized within a matrix with an oxygen-sensitive fluorescent dye. The immobilized enzyme reacts with the analyte and there is a consumption of oxygen. This reduction in oxygen is measured by the oxygen sensitive dye and is related to the concentration of the analyte. Examples are given in Table 6.

TABLE 6

| Analyte | Enzyme | $O_2$ Dye |
|---|---|---|
| Glucose | Glucose oxidase | Ru(dpp) |
| Lactate | Lactate oxidase | Ru(dpp) |

With regard to optical immunosensors or immunoprobes, which are not strictly reversible due to the high affinity between the antibody and the antigen, the antibody is immobilized within a matrix or on a support and a fluorescently labeled antigen is allowed to bind to the antibody. The association of the antigen with the antibody causes an increase in the fluorescence of the probe.

The devices and method of the invention are also applicable to molecular beacon type optical sensors which can be used to detect DNA base pairs. The operating principle is that a fluorophore and a quencher are attached to a strand of DNA and located in close proximity to each other so that no fluorescence is observed. When a complimentary DNA base pair is present, it binds to the DNA strand, resulting in the fluorophore and the quencher becoming separated. As the quencher molecule is now no longer close enough to the fluorophore to quench the fluorescence, there is an increase in fluorescence caused by the binding of the DNA base pair. For this kind of sensor and indicator system, the DNA strand containing the fluorophore and the quencher is immobilized on the sensor substrate while the complementary DNA base pair is the analyte.

Accordingly, numerous variations in optical sensing methods and strategies are applicable with the new TFELD-activated sensors and multisensor arrays taught herein. Each of these various systems, methods and apparatus for performing them are contemplated for use in the present invention.

EXAMPLE I

This example provides an all-organic miniature solid-state oxygen-sensing platform. The sensor is a thin film of tris(4,7-biphenyl-1,10-phenanthroline)Ru(II) Chloride (Ru(dpp)) immobilized within a porous sol-gel matrix, the photoluminescence (PL) intensity and lifetime of which are quenched by molecular oxygen. It is applied directly onto the back surface of one form of TFELD which is a blue organic light-emitting device (OLED), which provides pulsed excitation for the Ru(dpp).

Fabrication of the OLEDs. The OLED's structure is given in F. Li, H. Tang, J. Anderegg, and J. Shinar, Appl. Phys. Lett. 70, p. 1233 (1997); and H. Tang, F. Li, and J. Shinar, ibid 71,2560 (1997). The hole-injecting anode was ~2000 Å thick transparent 20 Ω/sq Applied Films Corp. indium tin oxide (ITO) film on a glass substrate. A 25 nm thick hole transporting layer of triphenyl diamine (TPD) followed by a 50 nm thick emitting layer of 4,4'-bis(2,2'biphenylvinyl)-1,1'biphenyl (DPVBi) were deposited on the ITO by thermal evaporation. See S. E. Shaheen, G. E. Jabbour, M. M. Morrell, Y. Kawabe, B. Kippelen, N. Peygham-barian, M. F. Nabor, R. Schlaf, A. Mash and N. R. Armstrong, J. Appl. Phys. 84, p.2324 (1998). These were followed by a ~20 Å thick $Al_2O_3$ buffer layer and the electron-injecting Al metal layer. The details on ITO cleaning and pretreatment as well as the preparation of the $Al_2O_3$ layer are in Li et al. and Tang et al., cited above. The aluminum electrodes were prepared as an array of round spots of 1.5 mm diameter; the 5×5 cm substrate included about 200 OLEDs.

Fabrication of the sensor films. Ru(dpp) was chosen since its absorption spectrum coincides with the blue OLED electroluminescence (EL), while its PL spectrum exhibits a large Stokes shift (~120 nm) permitting spectral resolution from the OLED excitation. The sol-gel glass matrix was chosen for immobilization of the oxygen sensitive dye as it is porous, chemically inert, optically transparent in the visible region and is synthesized under mild conditions. In addition, sol-gel processing is an extremely versatile technology so that it can be utilized for the production of monoliths, thin films and optical fibers.

Ru(dpp) was purchased from GFS; all other reagents were purchased from Aldrich. Sol-gel sensors, with a water to silicon alkoxide ratio r=2 containing immobilized Ru(dpp), were prepared using a spin-coating procedure. The silicon alkoxide precursor, methyltriethoxysilane (MTEOS) (0.5 ml) was mixed with water (0.09 ml) which had been adjusted to a pH of 1 using HCl, and ethanol (0.5 ml) which was used as a co-solvent, to produce a silica sol. The silica sol was stirred for two hours; Ru(dpp) at a concentration of 10 mg/ml was added half way through this period. The sol was then aged overnight at 70° C. to promote hydrolysis and condensation prior to coating. The sol-gel films were coated onto glass microscope cover-slips which had previously been silanized in a 2% solution of aqueous 3-(trimethoxysilyl) propylmethacrylate adjusted to pH 3.45 and then rinsed sequentially with deionized water and ethanol. The clean glass cover-slip was placed on the sample holder of a home-made spin-coater and 100 μl of Ru(dpp) doped sol-gel mix was pipetted onto the cover slip which was then spun at 1750 rpm for 30 seconds. The resulting optically transparent, crack-free sol-gel thin film was dried overnight in a covered Petri dish at 70° C.

Characterization. The excitation and absorption spectra were measured using a Fluoromax fluorimeter and UV 1604 Shimadzu spectrometer. The PL and electroluminescence (EL) spectra were measured using an Olympus inverted microscope, monochromator and Hammamtsu CCD camera system. Oxygen (>99%) and Nitrogen (>99%) were taken from a cylinder and a specially designed transparent flow-cell was employed. The sensor signal was detected in the direct transmission mode with the sensor facing the microscope objective.

Figure 9:
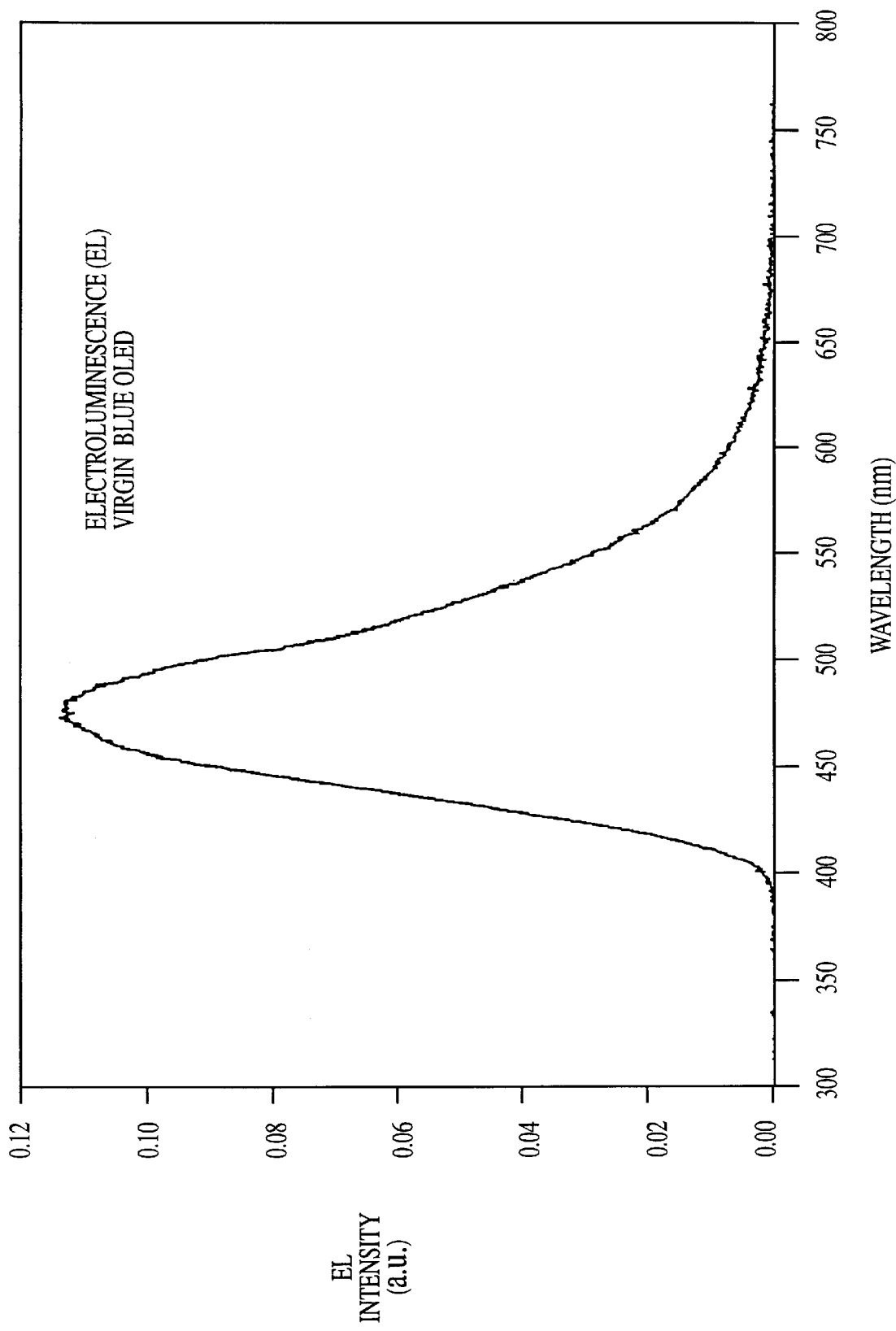
FIG. 9 shows the electroluminscence of a blue OLED under a pulsed bias.

Operation. To obtain the highest stable EL output the OLEDs were operated in a pulsed mode with a pulse width of 1–7 μsec, an amplitude of 28–31 V, and a repetition rate of 13–120 kHz. The EL spectrum obtained with a pulsed bias as shown in FIG. 9 was identical to the DC spectrum. Its emission maximum is at 475 nm and its FWHM is 95 nm. All of the OLEDs in the array exhibited identical EL spectra.

Figure 10:
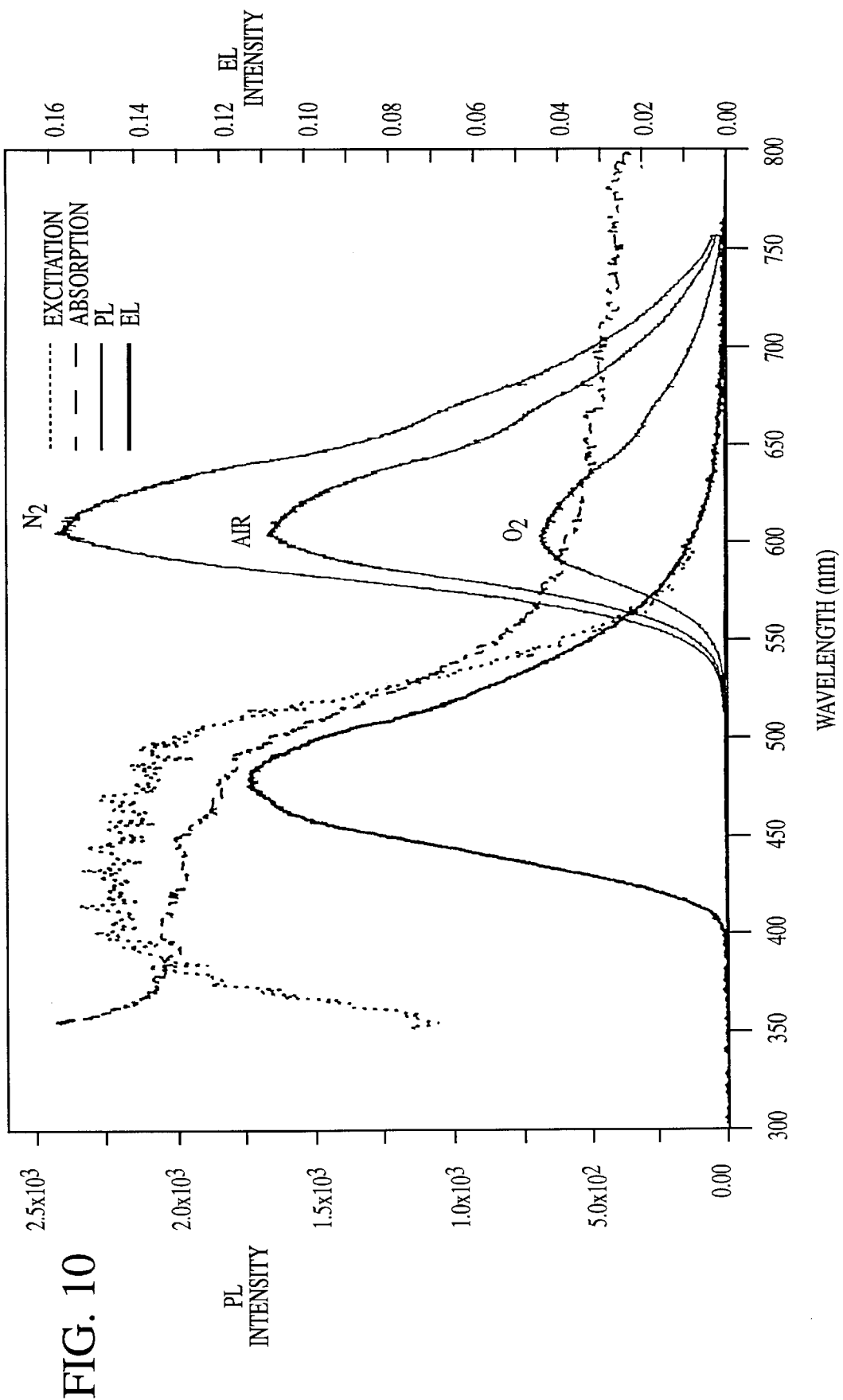
FIG. 10 shows the excitation, absorption, and PL spectra of an Ru(dpp) dye immobilized within a sol-gel matrix. The PL is shown in three environments, namely $N_2$, air, and $O_2$, and EL emission of the OLED.

FIG. 10 presents the excitation, absorption and emission spectra of Ru(dpp) immobilized in the sol-gel matrix, as well as the normalized EL spectrum of the virgin OLED. The Ru(dpp) film was spin-coated on glass to produce a thin film. The PL spectrum was obtained by excitation with a halogen lamp on an inverted microscope system. The broad lamp emission was filtered by a 450±25 nm band pass filter to mimic the blue OLED emission. As the figure shows, the Ru dye displays a strong Stokes shift when excited in the 400–520 nm region, as the PL peaks at ~610 nm. It also demonstrates that the EL strongly overlaps the Ru(dpp) PL excitation and absorption spectra, but there is little overlap between the EL and the sensor emission. Hence, by introducing a simple optical filter, it is possible to isolate the PL of the sensor from the EL of the OLED.

Figure 11:
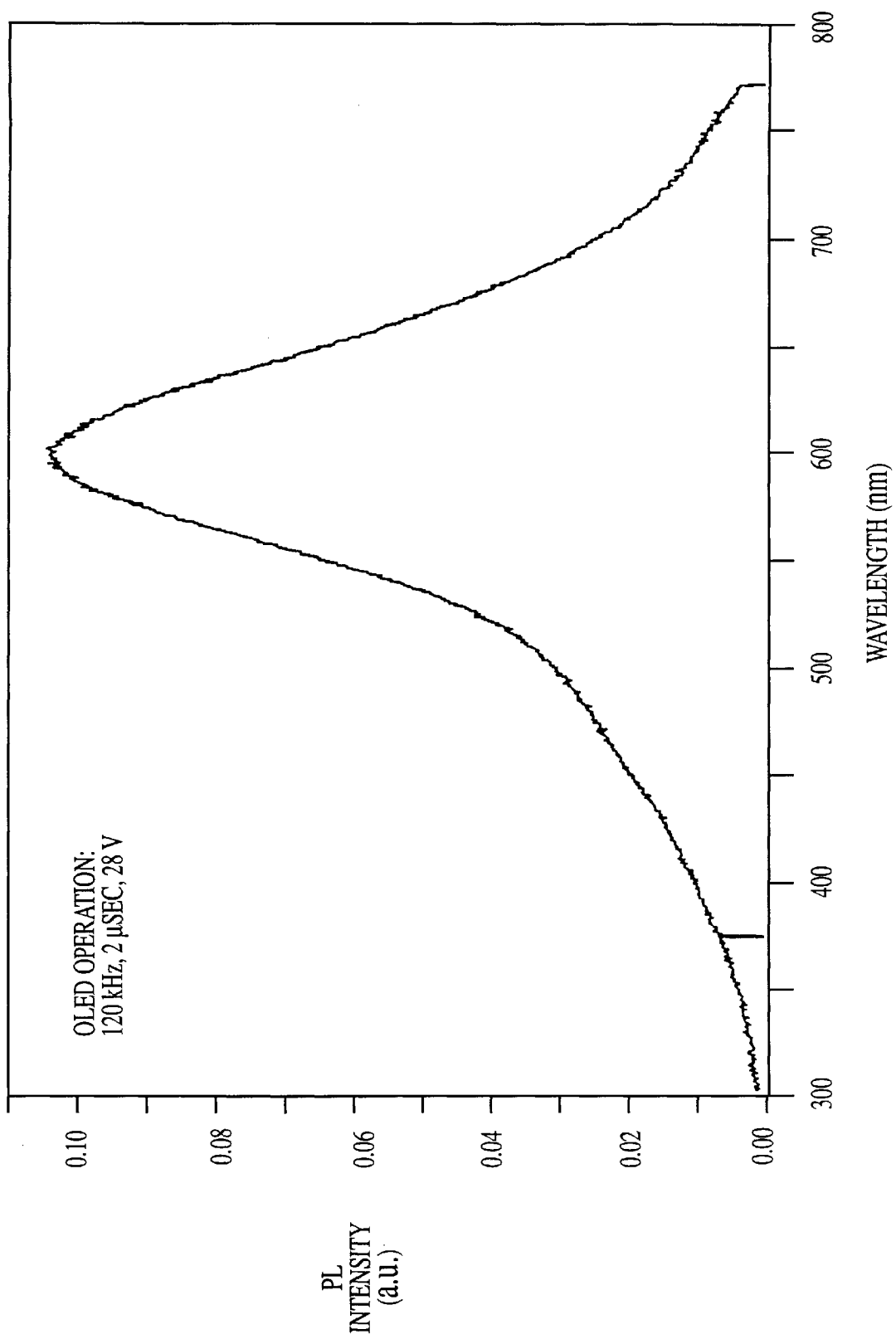
FIG. 11 shows the PL of an Ru(dpp) oxygen sensor excited by a blue OLED and collected in direct transmission mode. The OLED was operated in a pulsed mode.

The dye-sol-gel mixture was deposited by a capillary pipette on the other side of the OLED glass substrate. It was then left to dry for 5 minutes, resulting in a film that covered 2–3 OLEDs. The dye concentration was 5 mg/ml. The measurements were carried out on an inverted Olympus microscope system. The glass substrate also served as a cover of the flow cell, so the PL was collected through its transparent glass bottom. A typical PL spectrum of the sensor excited with a blue OLED in air is shown in FIG. 11. The objective was focused about ½ mm from the OLED edge. The PL spectrum was completely resolved at a frequency of 120 kHz, 2 μsec pulse width, and OLED bias of 28V. The results were reproducible with different OLEDs on the same array. It should be noted that although no filter was used to block the OLED emission, only a weak trace of the EL is observable, appearing as a slight broadening of the detected emission. This implies that the EL is almost completely absorbed by the sensor layer.

Figure 12:
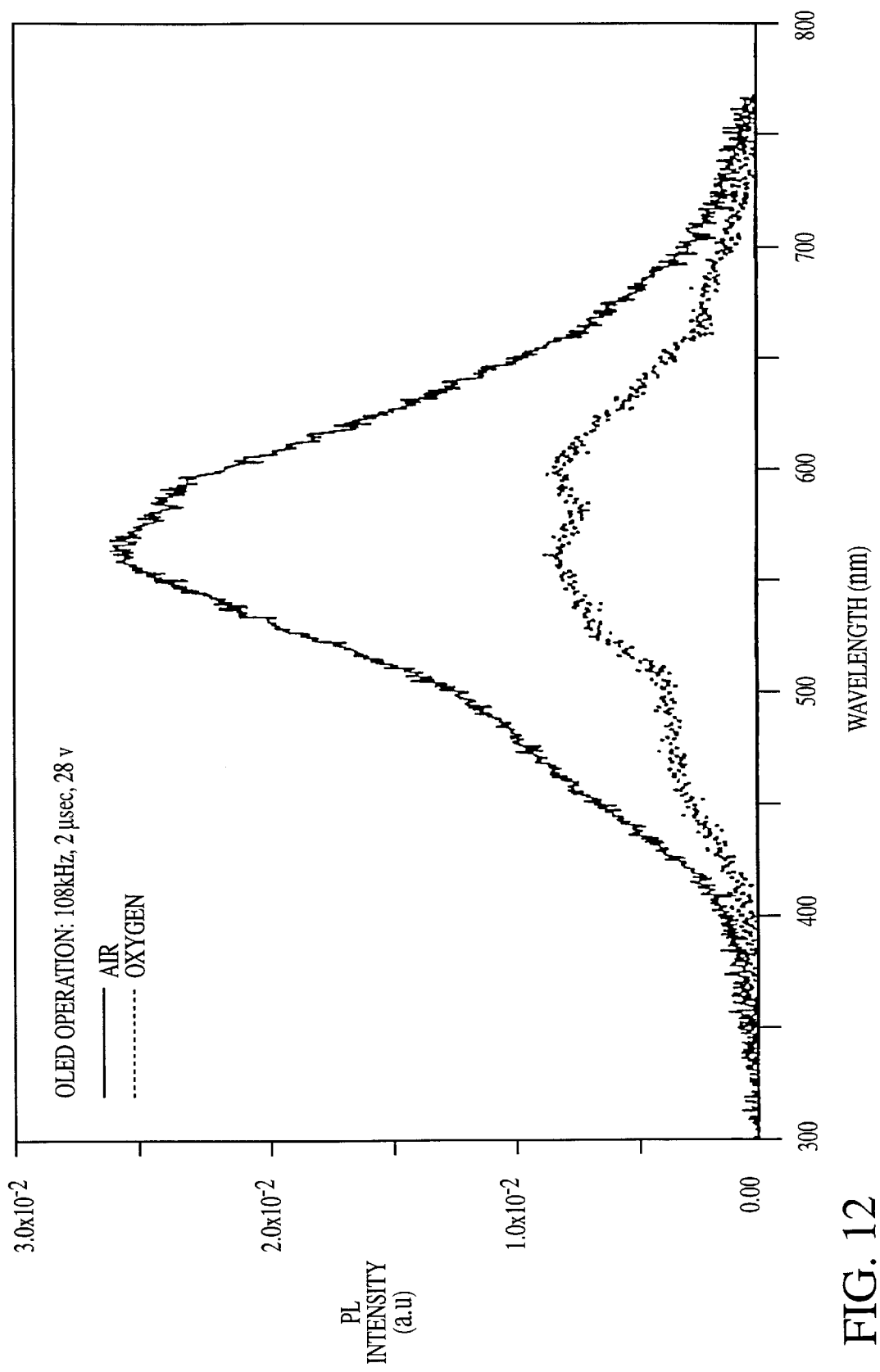
FIG. 12 shows the change in PL intensity of an Ru(dpp) oxygen sensor as a reaction to change in oxygen concentration, excited by a blue OLED, and collected in direct transmission mode. The OLED was operated in a pulsed mode.

The results obtained with the sensor/OLED system connected to a PL intensity measuring system are shown in FIG. 12. They demonstrate strong changes in I induced by sensor exposure to different gaseous environments.

The results demonstrate realization of a new sensing approach by a simple, portable measurement device, which is highly practical. Its further transformation into a lifetime-based sensor (Example II) results in a device that is fully integrated, inert sensing (no analyte consumption), self-calibrated, miniature, flexible, and inexpensive to the point of being disposable.

EXAMPLE II

Figure 13:
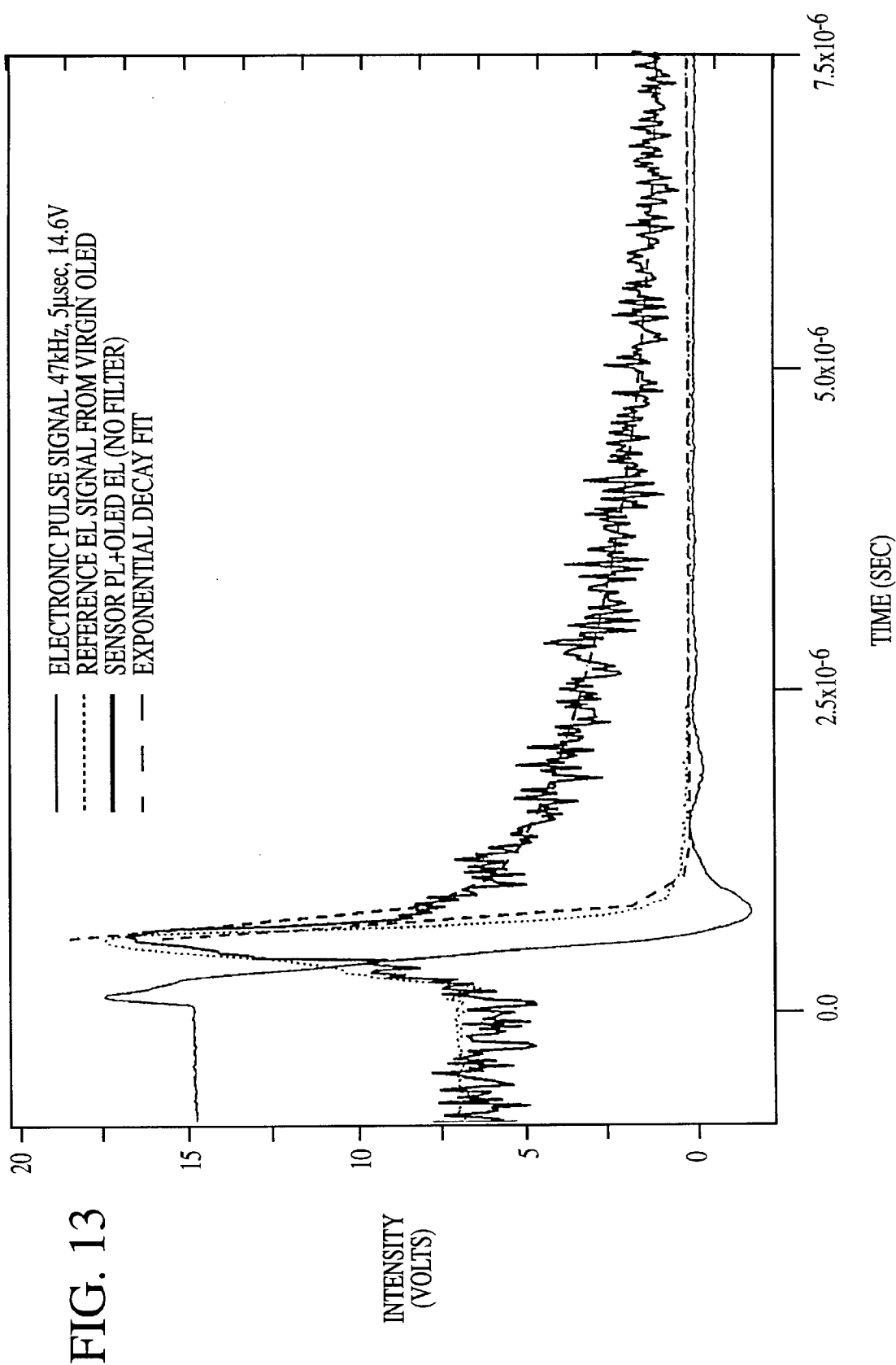
FIG. 13 shows time-resolved PL and EL collected in direct transmission mode according to one embodiment of the invention.

A. Time-resolved blue OLED electroluminescence and sensor photoluminescence in direct transmission mode in air:

The first experiment to detect time-resolved PL and EL was done without using any optical filter, and using capillary sensor deposition. The results are shown in FIG. 13. In the figure are shown the reference pulse signal from a pulse generator, the EL from a virgin OLED taken prior to sensor deposition, and the overall from the OLED and the sensor, as well as exponential decay fit. The lifetimes indicated in the figure were obtained from the best fit. The detection was done with an air-coOLED PMT and a Tektronix digital oscilloscope. The Ru(dpp) oxygen sensor deposition was done with a capillary pipette, sensor concentration 20 mg/ml. The Blue OLED used was a small diameter (1.5 mm) OLED from an array of 100 OLEDS.

When excited by a train of rectangular voltage pulses, bi-layer organic OLEDs like those used in this experiment emit a bright light flash synchronized with the voltage turn-off of each pulse. The flash brightness may exceed the steady state brightness of the OLED manifold (fourfold for the case in FIG. 14). The light flash decays had a characteristic time not exceeding 150 ns.

The Virgin Blue OLED exhibited a lifetime of 110 nanosec with the best fit of single exponential decay. The total signal from the OLED and the sensor exhibited a striking difference, having a strong long-lived tail. The long lived component of the signal was 2.3 microsec, which is typical of the Ru(dpp) decay time. The second short-lived component was associated with the OLED EL, since no optical filter was used in this set-up and both short lifetimes obtained from the best fits are matching, about 100–150 nanosec.

Figure 14:
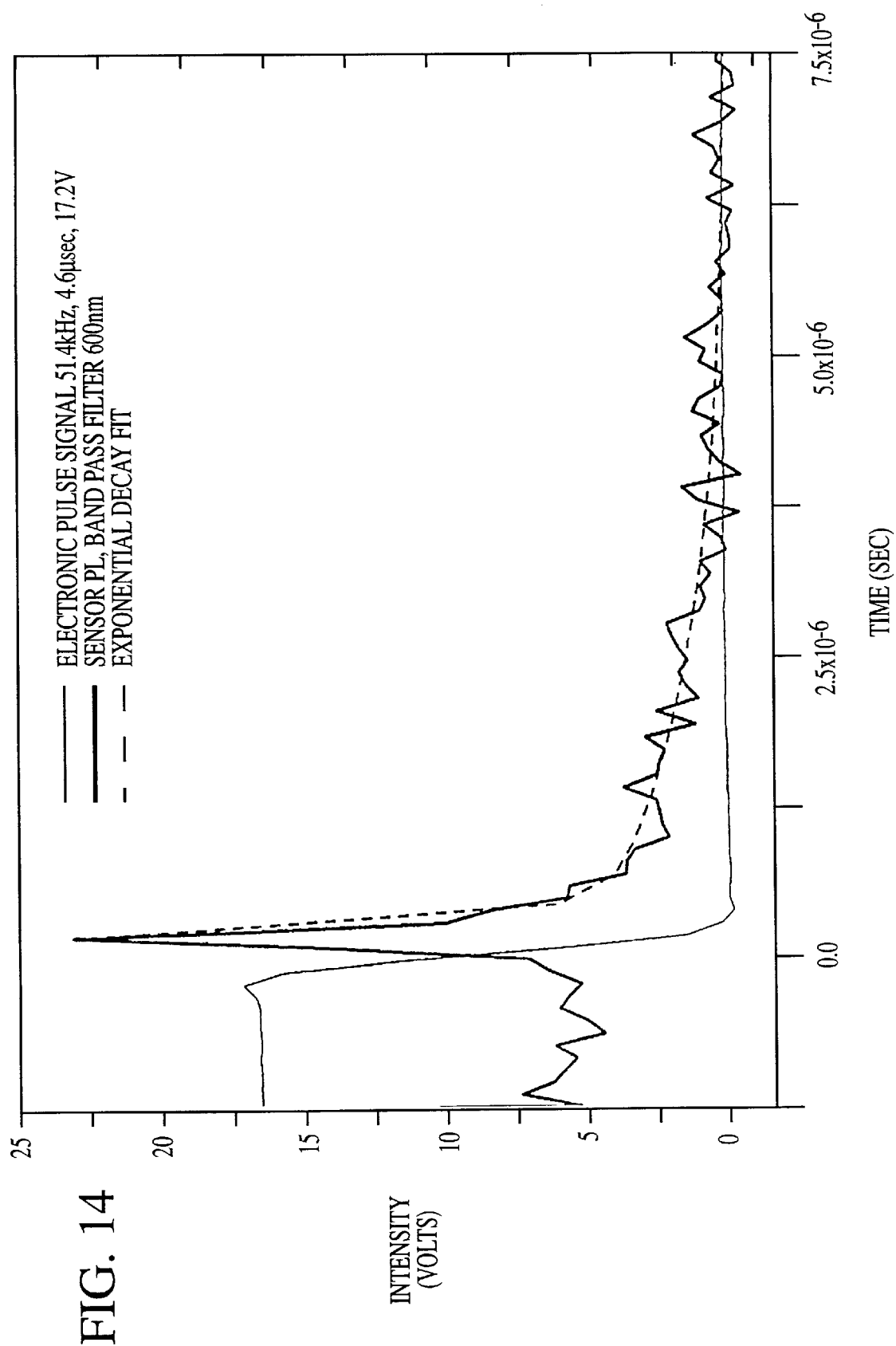
FIG. 14 shows time-resolved and spectrally-resolved PL and EL collected in direct transmission mode using a band-pass 600±15 nm filter according to yet another embodiment of the invention.

B. EL and PL time- and spectrally-resolved:

The results shown in FIG. 14 were recorded utilizing a wide band-pass filter of 600±15 nm (center of the Ru(dpp) emission is at 610 nm, see FIG. 14) to achieve complete spectral separation of OLED and sensor emission.

In the figure are shown the reference pulse signal from the pulse generator, the PL signal from the sensor, the exponential decay fit, and the lifetimes (those indicated in the figure were obtained from the best fit). The long-lived component exhibited a lifetime of 1.9 microsec. The short-lived component of about 100 nanosec is probably associated with the OLED decay, since OLED emission has a long tail up to 650 nm, partially overlapping the sensor emission (OLED emission is centered at 475 nm, see FIG. 10). Another possibility is that Ru(dpp) dye, entrapped in the sol-gel matrix, has a double exponential decay phenomenon, well known and described in the literature.

C. EL and PL time- and spectrally resolved, with spin-coated sensor:

In order to achieve improved performance, an Ru(dpp) oxygen sensor was produced using a spin-coating procedure. The sensor was coated on one side of a thin cover-slip (dye concentration 20 mg/ml) and the cover-slip was placed adjacent to the OLED glass substrate. All other experimental details were as described above, including the use of the band-pass 600 nm filter.

Figure 15:
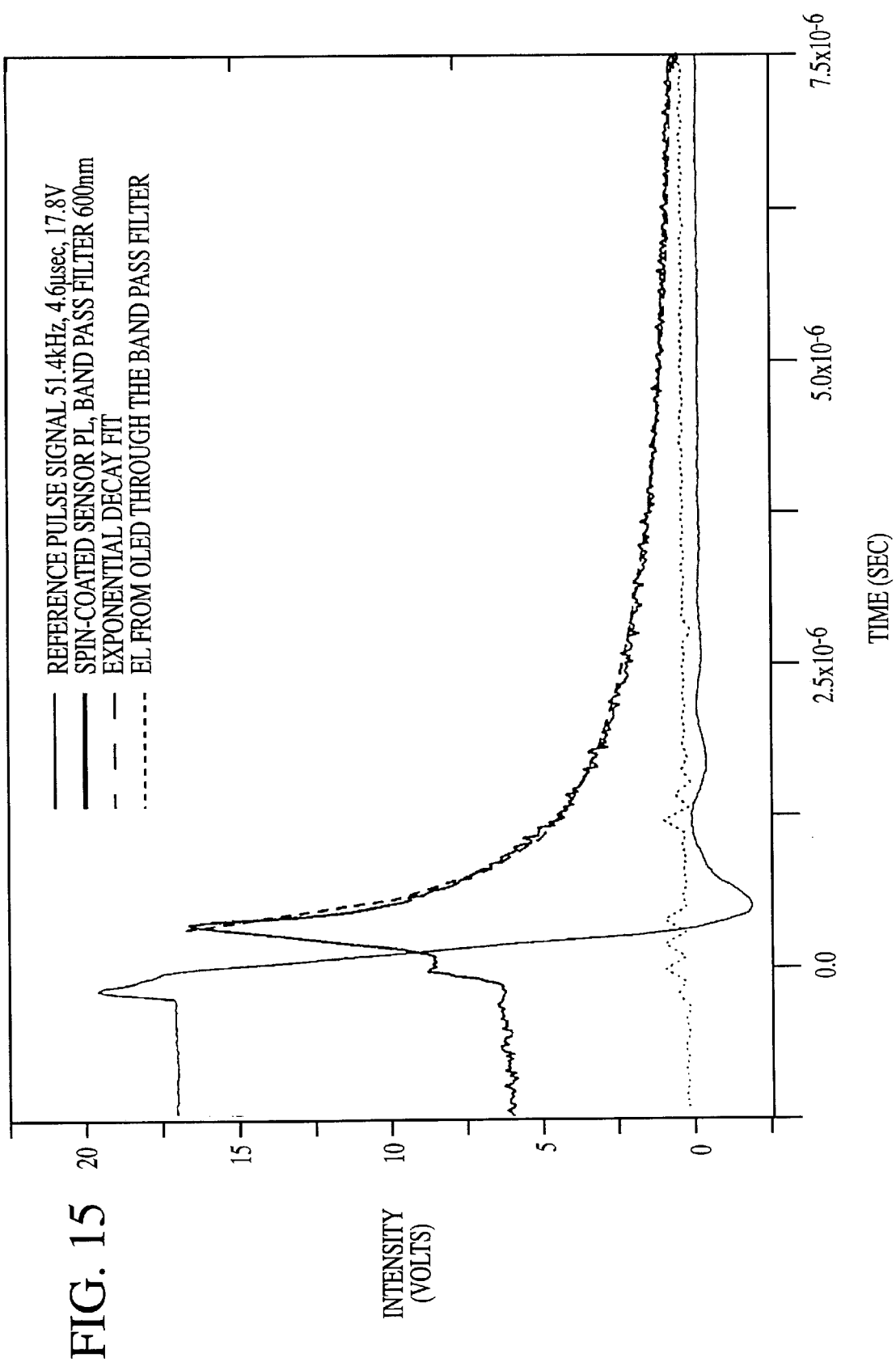
FIG. 15 shows time-resolved and spectrally-resolved PL and EL of a spin-coated sensor collected in direct transmission mode using a band-pass filter, 600±15 nm.

The results are shown in FIG. 15, including the reference pulse signal from pulse generator, the PL signal from the sensor, the exponential decay fit, and the lifetimes (indicated in the figure from the best fit). The long-lived component exhibited a lifetime of 2 microsec. The short-lived component lifetime was about 290 nanosec.

D. Time- and spectrally resolved blue OLED electroluminescence and sensor photoluminescence in back detection mode:

The sensor was applied by a capillary technique. A large-area (1 cm diameter) Blue OLED was used with a small hole made in the center of the non-transparent electrode, creating a ring geometry. By introducing a mirror in front of the sensor to reflect additional PL back to the detector, the signal intensity increased. To resolve the PL emission, a high-pass 550 nm filter was used.

Figure 16:
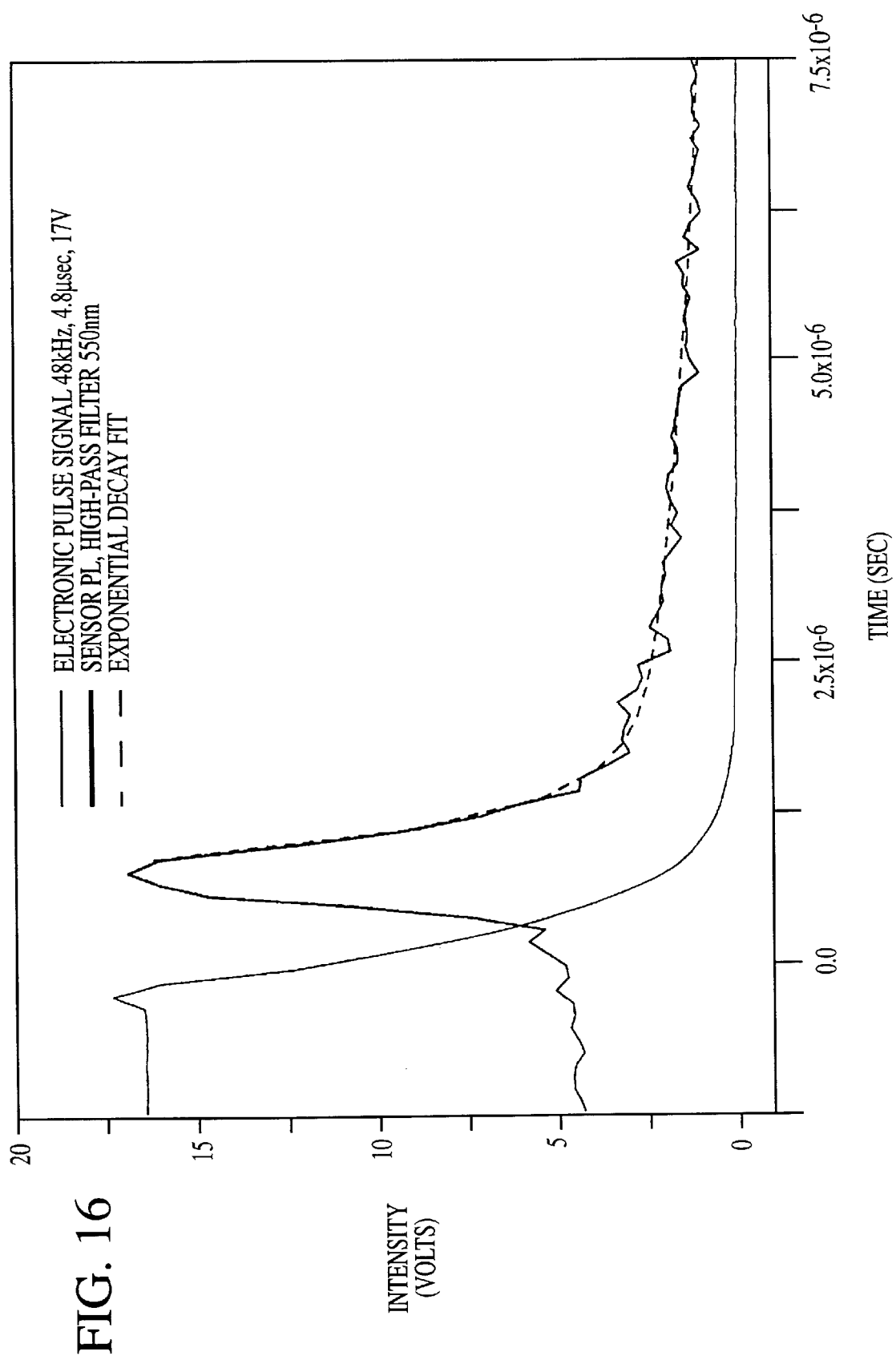
FIG. 16 shows the time-resolved and spectrally-resolved PL and EL collected in back detection mode using a high-pass 550 nm filter.

The results are shown in FIG. 16, including the reference pulse signal from the pulse generator, the PL signal from the sensor, the exponential decay fit, and the lifetimes (indicated in the figure from the best fit). The long-lived component exhibited a lifetime of 4.2 microsec. The short-lived component lifetime was about 270 nanosec.

The short-lived component of 270 nanosec again can be associated either with the OLED decay, which partially overlaps the sensor emission, or inherent double exponential decay of the entrapped Ru(dpp) dye. The long-lived component is in the microsecond range, as in previous results.

E. Conclusion: We directly observed the long-lived component of Ru(dpp) emission in the overall luminescence of the sensor/TFELD device both in direct transmission and in back detection modes. Spectral separation of EL and PL components demonstrated that the long lived component (1–2 µsec) is associated with Ru(dpp) fluorescence. The TFELD decay occurs in nanosecond scale (100–300 nanosec).

All patents and publications cited herein are incorporated by reference. It should be readily understood that the invention is not limited to the specific embodiments described and illustrated above. Rather, the invention can be modified to incorporate any number of analytes, indicator agents, sensing strategies, transmission geometries, peripheral apparatus, and other variations, alterations, substitutions or equivalent arrangements not heretofore described, which are commensurate with the spirit and scope of the invention. Accordingly, the invention is not limited by the forgoing description, but is only limited by the scope of the appended claims.

What is claimed as new and desired to be protected by Letters Patent of the United States is:

1. An optical sensor for detecting an analyte of interest in a sample, said optical sensor comprising;
   a sensing layer containing an indicator agent which can react optically with said analyte,
   a thin film electroluminescent device comprising a luminescent layer which emits light of a predetermined wavelength, wherein said luminescent layer is optically coupled to said sensing layer,
   wherein said indicator agent absorbs light energy of said predetermined wavelength and in the presence of at least one analyte of interest generates an optical response which is optically detectable and recognizable as indicating the presence of the analyte of interest, and
   wherein said thin film electroluminescent device comprises an organic electroluminescent material.

2. An optical sensor according to claim 1, further comprising a photodetector.

3. An optical sensor according to claim 2, wherein said photodetector is selected from the group consisting of a photodiode, a photomultiplier tube, a charge injection device, a charged couple device (CCD) array, or a CMOS based imager.

4. An optical sensor according to claim 1, further comprising a pulse generator capable of pulsed excitation of said thin film electroluminescent device.

5. An optical sensor according to claim 1, further comprising a substrate, wherein said sensing layer is on one surface of said substrate and said thin film light emitting device is on an opposing surface of said substrate.

6. An optical sensor according to claim 1, wherein said thin film electroluminescent device is substantially transparent.

7. An optical sensor according to claim 1, wherein said luminescent layer comprises a material selected from the group consisting of 4',4'-bis(2,2'biphenylvinyl)-1, 1'biphenyl; 8-tris-(hydroxy quinoline); 4,4'-N,N'-dicarbazolyl biphenyl; and distyrylarylenes.

8. An optical sensor according to claim 1, wherein said indicator agent is selected from the group consisting of dyes, polymers, and biological receptors.

9. An optical sensor according to claim 1, wherein said indicator agent comprises tris(4,7-biphenyl-1,10-phenanthroline) Ru(dpp) (II).

10. An optical sensor according to claim 1, wherein said sensing layer further comprises a sol-gel.

11. An optical sensor according to claim 1, wherein said sensing layer further comprises a matrix of polymeric material.

12. An optical sensor according to claim 1, wherein said thin film electroluminescent device comprises a material selected from the group consisting of polycrystalline zinc sulfide and polycrystalline zinc selenide.

13. An optical sensor according to claim 1, wherein said thin film electroluminscent device has a thickness of less than about 1 micron.

14. An optical sensor according to claim 1, wherein said analyte is selected from the group consisting of oxygen, ions, antibodies, antigens, nucleotides, and microbial receptor proteins.

15. An optical sensor according to claim 1, wherein said sensor comprises an array of sensors or probes.

16. An optical sensor according to claim 1, wherein said sensor is an ion correlation sensor and said indicator agent comprises an ionophore.

17. An optical sensor according to claim 16 further comprising an indicator agent selected from the group consisting of a voltage sensitive dye and a chromoionophore.

18. An optical sensor according to claim 1, wherein said sensor is an enzymatic sensor and said indicator agent comprises an enzyme.

19. An optical sensor according to claim 18, wherein said enzyme is co-immobilized within a matrix with an oxygen-sensitive dye.

20. An optical sensor according to claim 1, wherein said sensor is an immunosensor and said indicator agent comprises an antibody or antigen.

21. An optical sensor according to claim 1, wherein said sensor is a molecular beacon sensor and said indicator agent comprises a nucleotide sequence.

22. An optical sensor according to claim 21, further comprising a fluorophore and a quencher attached to said sequence.

23. An optical sensor according to claim 22, wherein said analyte is a second nucleotide sequence complementary to said nucleotide sequence.

24. An optical sensor according to claim 1, wherein said luminescent layer comprises a material selected from the group consisting of poly(3-alkylthiophenes), poly(p-phenylenevinylenes), poly(p-phenylenes), and poly(alkylfluorenes).

25. An optical sensor array for detecting at least one analyte of interest in a fluid sample, said optical sensor array comprising:
  a plurality of sensing units at least some of which differ in their chemical formulations and their optical characteristics, which react optically differently with an individual analyte of interest, each of said sensing units of said array including:
    a sensing layer containing an indicator agent,
    a thin film electroluminescent device having a luminescent layer which emits light of a predetermined wavelength,
    wherein said indicator agent absorbs light energy of said predetermined wavelength and in the presence of at least one analyte of interest generates an optical response which is detectable and recognizable as showing the presence of the analyte of interest, and wherein said thin film electroluminescent device comprises an organic electroluminescent material.

26. An optical sensor array according to claim 25, further comprising a detector selected from the group consisting of a charge coupled device CCD array, a CMOS based imager, and a charge injection device capable of detecting the optical responses of a plurality of sensing units of said array.

27. An optical sensor array according to claim 25, further comprising a plurality of thin film electroluminescent devices capable of emitting light of a plurality of different wavelengths.

28. An optical sensor array according to claim 27, wherein said plurality of thin film electroluminescent devices are arranged in a stacked configuration.

29. An optical sensor according to claim 25, further comprising a pulse generator capable of pulsed excitation of said thin film electroluminescent device.

30. An optical sensor array according to claim 25, further comprising a substrate, wherein said sensing layer is on one surface of said substrate and said thin film light emitting device is on an opposing surface of said substrate.

31. An optical sensor array according to claim 25, wherein said thin film electroluminescent device is substantially transparent.

32. An optical sensor array according to claim 25, wherein said thin film electroluminescent device comprises a first and a second hole transporting layer.

33. An optical sensor array according to claim 32, wherein at least one of said hole transporting layers comprises a material selected from the group consisting of 4,4',4"-tris(N-(3-methoxyphenyl)-N-phenyl-amine-triphenylamine); MTDATA; copper phthalocyanine; N,N',biphenyl-N,N'bis(2-methylphenyl)-(1,1'-biphenyl)-4,4'-diamine; and N,N'-biphenyl-N,N'-bis(1-naphthyl)-1,1'-biphenyl-4,4'-diamine.

34. An optical sensor array according to claim 25, wherein said luminescent layer comprises a material selected from the group consisting of 4',4'-bis(2,2'biphenylvinyl)-1,1'bipheny; 8-tris-(hydroxy quinoline); 4,4'-N,N'-dicarbazolyl biphenyl; and distyrylarylene.

35. An optical sensor array according to claim 25, wherein said indicator agent is selected from the group consisting of dyes, polymers, and biological receptors.

36. An optical sensor array according to claim 25, wherein said indicator agent comprises tris(4,7-biphenyl-1, 10-phenanthroline) Ru(dpp) (II).

37. An optical sensor array according to claim 25, wherein said sensing layer further comprises a sol-gel.

38. An optical sensor array according to claim 25, wherein said sensing layer further comprises a matrix of polymeric material.

39. An optical sensor array according to claim 25, wherein said thin film electroluminescent device comprises a material selected from the group consisting of polycrystalline zinc sulfide and polycrystalline zinc selenide.

40. An optical sensor array according to claim 25, wherein said thin film electroluminscent device has a thickness of less than about 1 micron.

41. An optical sensor array according to claim 25, wherein said analyte is selected from the group consisting of oxygen, ions, antibodies, antigens, nucleotides, and microbial receptor proteins.

42. A kit comprising a plurality of optical sensors for detecting the presence of one or more analytes of interest in a sample, each sensor comprising:

an anode, a hole transporting layer, an electron transporting layer, and a cathode, wherein said cathode and anode are capable of activating the emission of electroluminescence of a predetermined wavelength from either said hole transporting layer or said electron transporting layer;

a sensing layer optically coupled to said electroluminescent hole or electron transporting layer, wherein said sensing layer contains an indicator agent that absorbs light of said predetermined wavelength and generates an optical response that is dependent upon the absence or presence of said analyte; and a detector for detecting the optical response from said sensing layer.

43. A kit according to claim 42, wherein at least one of said plurality of sensing layers further comprises a polymeric material and wherein said indicator agent is dispersed in said polymeric material.

44. A kit according to claim 42, wherein said indicator agent of at least one of said plurality of sensors comprises a Ruthenium complex.

45. A kit according to claim 42, wherein said electroluminescent layer is substantially transparent to said optical response of said indicator agent.

46. A kit according to claim 42, wherein said electroluminescent layer comprises a material selected from the group consisting of 4',4'-bis(2,2' biphenylvinyl)-1,1' biphenyl; 8-tris-(hydroxy quinoline); 4,4'-N,N'-dicarbazolyl biphenyl; distyrylarylenes; 4,4',4"-tris(N-(3-methoxyphenyl)-N-phenyl-amine-triphenylamine); MTDATA; copper phthalocyanine; N,N',biphenyl-N,N'bis(2-methylphenyl)-(1,1'-biphenyl)-4,4'-diamine; N,N'-biphenyl-N,N'-bis(1-naphthyl)-1,1'-biphenyl-4,4'-diamine; poly(3-alkylthiophenes); poly(p-phenylenevinylenes); poly(p-phenylenes); and poly(alkylfluorenes).

47. A kit according to claim 42, further comprising a pulse generator and wherein said optical response is activated by pulsed excitation.

48. An optical method for detecting an analyte of interest in a fluid sample, said method comprising:

providing an optical sensing unit containing a sensing layer, and a thin film electroluminescent device wherein said sensing layer can absorb light of a predetermined wavelength and provide an optical response specific to the presence of an individual analyte of interest;

introducing a sample to contact said sensing layer;

activating said thin film electroluminescent device to emit light energy of said predetermined wavelength to said sensing layer;

optically detecting said optical response of said sensing layer;

evaluating said response to determine the presence or concentration of at least one analyte of interest in the sample; and wherein said thin film electroluminescent device comprises an organic electroluminescent material.

49. A method according to claim 48, wherein said detection is conducted on the same side of said sensing unit as said thin film electroluminescent device.

50. A method according to claim 48, wherein said thin film electroluminescent device is transparent to said specific optical response.

51. A method according to claim 48, further comprising an array of optical sensing units for detecting a plurality of different analytes.

52. A method according to claim 48, wherein said detection is conducted using a detector selected from the group consisting of a CCD array or camera, a CMOS based imager, and a charge injection device.

53. A method according to claim 48, further comprising the step of reflecting said optical response back through said electroluminescent device.

54. A method according to claim 48, further comprising a pulse generator capable of pulse excitation of said thin film electroluminescent device.

55. A method according to claim 48, further comprising a transparent substrate, wherein said sensing layer is on one surface of said substrate and said thin film light emitting device is on an opposing surface of said substrate.

56. A method according to claim 51, wherein said thin film electroluminescent device is substantially transparent.

57. A method according to claim 48, wherein said thin film electroluminescent device comprises a hole transporting layer.

58. A method according to claim 48, wherein said electroluminescent device comprises a material selected from the group consisting of 4',4'-bis(2,2'biphenylvinyl)-1, 1'biphenyl; 8-tris-(hydroxy quinoline); 4,4'-N,N'-dicarbazolyl biphenyl; and distyrylarylenes.

59. A method according to claim 57, wherein said hole transporting layer comprises a material selected from the group consisting of 4,4',4"-tris(N-(3-methoxyphenyl)-N-phenyl-amine-triphenylamine); MTDATA; copper phthalocyanine; N,N',biphenyl-N,N'bis(2-methylphenyl)-(1,1'-biphenyl)-4,4'-diamine; and N,N'-biphenyl-N,N'-bis(1-naphthyl)-1,1'-biphenyl-4,4'-diamine.

60. A method according to claim 48, wherein said indicator agent is selected from the group consisting of dyes, polymers, and biological receptors.

61. A method according to claim 48, wherein said sensing layer comprises tris(4,7-biphenyl-1, 10-phenanthroline) Ru(dpp) (II).

62. A method according to claim 48, wherein said sensing layer further comprises a sol-gel.

63. A method according to claim 48, wherein said sensing layer further comprises a matrix of polymeric material.

64. A method according to claim 48, wherein said thin film electroluminescent device comprises a material selected from the group consisting of polycrystalline zinc sulfide and polycrystalline zinc selenide.

65. A method according to claim 48, wherein said thin film electroluminscent device has a thickness of less than about 1 micron.

66. A method according to claim 48, wherein said analyte is selected from the group consisting of oxygen, ions, antibodies, antigens, nucleotides, and microbial receptor proteins.

67. A method according to claim 48, wherein said electroluminescent device comprises a material selected from the group consisting of poly(3-alkylthiophenes), poly(p-phenylenevinylenes), poly(p-phenylenes), and poly(alkylfluorenes).

68. An optical sensor for detecting an analyte of interest in a sample, said optical sensor comprising;

a sensing layer containing an indicator agent which can react optically with said analyte, a thin film electroluminescent device comprising a luminescent layer which emits light of a predetermined wavelength, wherein said luminescent layer is optically coupled to said sensing layer, wherein said indicator agent absorbs light energy of said predetermined wavelength and in the presence of at least one analyte of interest generates an optical response which is optically detectable and recognizable as indicating the presence of the analyte of interest, and wherein said thin film electroluminescent device comprises a first and a second hole transporting layer.

69. An optical sensor according to claim 68, further comprising a photodetector.

70. An optical sensor according to claim 69, wherein said photodetector is selected from the group consisting of a photodiode, a photomultiplier tube, a charge injection device, a charged couple device (CCD) array, or a CMOS based imager.

71. An optical sensor according to claim 68, further comprising a pulse generator capable of pulsed excitation of said thin film electroluminescent device.

72. An optical sensor according to claim 68, further comprising a substrate, wherein said sensing layer is on one surface of said substrate and said thin film light emitting device is on an opposing surface of said substrate.

73. An optical sensor according to claim 68, wherein said thin film electroluminescent device is substantially transparent.

74. An optical sensor according to claim 68, wherein said luminescent layer comprises a material selected from the group consisting of 4',4'-bis(2,2'biphenylvinyl)-1,1'biphenyl; 8-tris-(hydroxy quinoline); 4,4'-N,N'-dicarbazolyl biphenyl; and distyrylarylenes.

75. An optical sensor according to claim 68, wherein at least one of said hole transporting layers comprises a material selected from the group consisting of 4,4',4"-tris(N-(3-methoxyphenyl)-N-phenyl-amine-triphenylamine); MTDATA; copper phthalocyanine; N,N',biphenyl-N,N'bis(2-methylphenyl)-(1,1'-biphenyl)-4,4'-diamine; and N,N'-biphenyl-N,N'-bis(1-naphthyl)-1,1'-biphenyl-4,4'-diamine.

76. An optical sensor according to claim 68, wherein said indicator agent is selected from the group consisting of dyes, polymers, and biological receptors.

77. An optical sensor according to claim 68, wherein said indicator agent comprises tris(4,7-biphenyl-1, 10-phenanthroline) Ru(dpp) (II).

78. An optical sensor according to claim 68, wherein said thin film electroluminscent device has a thickness of less than about 1 micron.

79. An optical sensor according to claim 68, wherein said sensor comprises an array of sensors or probes.

80. A layered device for detecting an analyte, comprising:

a first layer comprising an indicating agent, said indicating agent having the capability of producing an optically detectable reaction in the presence of said analyte;

a second layer optically coupled to said first layer and comprising an organic material able to generate a light of a predetermined wavelength, wherein said light of a predetermined wavelength enables the optically detectable reaction of said indicating agent of said first layer; and a third layer optically coupled to said first layer and comprising a photodetector, wherein said third layer is on the opposite side of said second layer from said first layer.

81. The layered device of claim 80, wherein said organic material of said second layer comprises a material selected from the group consisting of 4',4'-bis(2,2'biphenylvinyl)-1,1' biphenyl; 8-tris-(hydroxy quinoline); 4,4'-N,N'-dicarbazolyl biphenyl; and distyrylarylenes.

82. The layered device of claim 80, wherein said indicating agent of said first layer comprises tris94,7-biphenyl-1, 10-phenanthroline) Ru(dpp)(II).

83. The layered device of claim 80, wherein said indicating agent is combined with a sol-gel.

84. The layered device of claim 80, wherein said indicating agent is combined with a polymeric matrix.

85. The layered device of claim 80, wherein said analyte to be detected is selected from the group consisting of oxygen, ions, antibodies, antigens, nucleotides, and microbial receptor proteins.

86. The layered device of claim 80, wherein said second layer comprises first and second hole sorting layers.

87. The layered device of claim 86, wherein at least one of said hole transporting layers comprises a material selected from the group consisting of 4,4',4"-tris(N-(3-methoxyphenyl-N-phenyl-amine-triphenylamine); MTDATA; copper phthalocyanine; N,N',biphenyl-N,N'bis(2-methylphenyl)-(1,1'-biphenyl)4,4'-diamine; and N,N'-biphenyl-N,N'-bis(1-naphthyl)-1,1'-biphenyl-4,4'-diamine.

88. The layered device of claim 80, further comprising a substrate, wherein said first layer is on one side of said substrate and said thin second layer is on an opposing side of said substrate.

89. The layered device of claim 81, wherein said second layer is substantially transparent.

90. The layered device of claim 80, wherein said second layer has a thickness of less than about 1 µm.

* * * * *